US007244586B2

(12) United States Patent
Cully et al.

(10) Patent No.: US 7,244,586 B2
(45) Date of Patent: Jul. 17, 2007

(54) DNA MOLECULES ENCODING LIGAND-GATED ION CHANNELS FROM DROSOPHILA MELANOGASTER

(75) Inventors: Doris F. Cully, Scotch Plains, NJ (US);
Birgit Priest, Long Valley, NJ (US);
Jeffrey Yuan, Plainsboro, NJ (US);
Yingcong Zheng, Colonia, NJ (US)

(73) Assignee: Merck & Co., Inc., Rahway, NJ (US)

( * ) Notice: Subject to any disclaimer, the term of this patent is extended or adjusted under 35 U.S.C. 154(b) by 785 days.

(21) Appl. No.: 10/204,029

(22) PCT Filed: Feb. 26, 2001

(86) PCT No.: PCT/US01/06096

§ 371 (c)(1),
(2), (4) Date: Aug. 15, 2002

(87) PCT Pub. No.: WO01/64705

PCT Pub. Date: Sep. 7, 2001

(65) Prior Publication Data

US 2005/0261487 A1   Nov. 24, 2005

Related U.S. Application Data

(60) Provisional application No. 60/186,645, filed on Mar. 2, 2000.

(51) Int. Cl.
*C07K 14/00* (2006.01)
*C07H 21/04* (2006.01)
*C12N 5/00* (2006.01)
*C12N 15/09* (2006.01)
*G01N 33/53* (2006.01)

(52) U.S. Cl. ................... 435/69.1; 435/7.1; 435/70.1; 435/235.1; 435/320.1; 435/325; 435/348; 530/350; 536/23.1

(58) Field of Classification Search ................ None
See application file for complete search history.

(56) References Cited

U.S. PATENT DOCUMENTS 5,527,703 A   6/1996   Cully et al.
5,693,492 A   12/1997  Cully et al.
5,854,002 A * 12/1998 Tomalski et al. ............ 435/7.2
6,703,491 B1 * 3/2004  Homburger et al. ....... 536/23.1

FOREIGN PATENT DOCUMENTS

WO   WO99/07828   2/1999

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Campbell et al. Totipotency of multipotentiality of cultured cells: applications and progress. Theriogenology 47: 63-72, 1997.*
Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Wigley et al. Site-specific transgene insertion: an approach. Reprod Fertil Dev 6: 585, 588, 1994.*
Phillips, A., The challenge of gene therapy and DNA delivery. J Pharm Pharmacology 53: 1169-1174, 2001.*
Adams et al. Genbank Accession No. AC18284, Dec. 9, 1999.*
Gisselmann et al. Unusual functional properties of homo- and heteromultimeric histamine-gated chloride channels of *Drosophila melanogaster*: spontaneous currents and dual gating by GABA and histamine. Neurosci Lett 372: 151-156, 2004.*
Bloomquist, JR. Chloride channels as tools for developing selective insecticides. Arch Insect Biochem Physiol. 54(4):145-156, 2003.*
Zheng et al. Genbank Accession No. 382401, Jan. 21, 2001.*
Geary, TG. Frontiers in anthelmintic pharmacology. Vet Parasitol. 84(3-4):275-295, 1999.*
Van Wyk et al. Anthelmintic resistance in South Africa: surveys indicate an extremely serious situation in sheep and goat farming. Onderstepoort J Vet Res. 66(4):273-284, 1999.*
Young et al. Parasite diversity and anthelmintic resistance in two herds of horses. Vet Parasitol. 85(2-3):205-14, 1999.*
Yin et al. AY049774, Jan. 11, 2003.*
Gisselman et al. Two cDNAs coding for histamine-gated ion channels in *D. melanogaster*. Nat Neurosci 5(1):11-12, 2002.*

(Continued)

*Primary Examiner*—Bridget Bunner
(74) *Attorney, Agent, or Firm*—Laura M. Ginkel; Sheldon O. Heber

(57) ABSTRACT

The present invention relates in part to isolated nucleic acid molecules (polynucleotides) which encode *Drosophila melanogaster* ligand-gated ion channel proteins. The present invention also relates to recombinant vectors and recombinant hosts which contain a DNA fragment encoding *Drosophila* ligand-gated ion channel proteins, substantially purified forms of associated *Drosophila* ligand-gated ion channel proteins and recombinant membrane fractions comprising these proteins, associated mutant proteins, and methods associated with identifying compounds which modulate associated *Drosophila melanogaster* ligand-gated ion channel proteins, which will be useful as insecticides.

27 Claims, 8 Drawing Sheets

OTHER PUBLICATIONS

Zajac et al. Multiple anthelmintic resistance in goat herd. Vet Parasitol. 87(2-3):163-172, 2000.*

Raymond et al. Novel animal-health drug targets from ligand-gated chloride channels. Nat Rev Drug Discov 1(6):427-436, 2002.*

Nassel et al. Histamine in the brain of insects: a review. Microsc Res Tech 44(2-3):121-136, 1999.*

Buchner et al. Histamine is a major mechanosensory neurotransmitter candidate in *Drosophila melanogaster*. Cell Tissue Res 273(1):119-125, 1993.*

Iochev et al. Altered drug resistance and recovery from paralysis in *Drosophila melanogaster* with a deficient histamine-gated chloride channel. Journal of Neurogenetics 16:249-261, 2002.*

Genbank Accession No. AJ000538, Dent, J.A. et al. "avr-15 Encodes a Chloride Channel Subunit that Mediates Glutamatergic Neurotransmission and ivermectin sensitivity in *C. elegans*", Nov. 15, 1997.

Arena, J. et al. "Avermectin-Sensitive Chloride Currents Induced by *Caenorhabditis elegans* RNA in Xenopus Oocytes". Molecular Pharmacology, vol. 40, 1991, pp. 368-374.

Stuart, A. "From Fruit Flies to Barnacles, Histamine Is the Neurotransmitter of Arthropod Photoreceptors". NEURON, vol. 22, 1999, pp. 431-433.

Lea, T. et al. "The Site of Action of Ibotenic Acid and the Identification of Two Populations of Glutamate Receptors on Insect Muscle-Fibres". Comp. Gen. Pharmac., vol. 4, 1973, pp. 333-350.

Lingle, C. et al. "A Glutamate-Activated Chloride Conductance on a Crustacean Muscle". Brain Research, vol. 212, 1981, pp. 481-488.

Horseman, B. et al. "The Effects of L-Glutamate on Cultured Insect Neurones". Neuroscience Letters, vol. 85, 1988, pp. 65-70.

Cully, D. et al. "Cloning of an Avermectin Sensitive Glutamate-Gated Chloride Channel from *Caenorhabditis elegans*". NATURE, vol. 371, 1994, pp. 707-711.

Cull-Candy, S. et al. "Two types of Extrajunctional L-Glutamate Receptors in Locust Muscle Fibres". J. Physiol, vol. 255, 1976, pp. 449-464.

Cully, D. et al. "Identification of a *Drosophila melanogaster* Glutamate-Gated Chloride Channel Sensitive to the Antiparasitic Agent Avermectin". The Journal of Biological Chemisty, vol. 271, No. 33, 1996, pp. 20187-20191.

Vassilatis, D. et al. "Genetic and Biochemical Evidence for a Novel Avermectin-sensitive Chloride Channel in *Caenorhabditis elegans*". The Journal of Biological Chemistry, vol. 272, No. 52, 1997, pp. 33167-33174.

O'Tousa, J. et al. "Morphological Defects in $ora_{JK84}$ Photoreceptors Caused by Mutation in RI-6 Opsin Gene of *Drosophila*". vol. 6, 1989, pp. 41-52.

Arena, J. et al. "Expression of a Glutamate-Activated Chloride Current in *Xenopus* Oocytes injected with *Caenorhabditis elegans* RNA: Evidence for Modulation by Avermectin". vol. 15, 1992, pp. 339-348.

Skingsley, D.R. etal.: "Properties of histamine-activated chloride channels in the large monopolar cells of the dipteran compound eye: A comparative study" Journal of Comparative Physiology A: Sensory Neural and Behavioral Physiology, vol. 176, No. 5, 1995, pp. 611-623.

EMBL-EBI UniProt Database ID No. Q9VGI0, "CG14723-PA, isoform A (Histamine-gated chloride channel subunit1),". Mar. 1, 2001.

EMBL-EBI UniProt Database ID No. Q9VDU9, "CG7411-PA (Histamine-gated chloride channel subunit 2)," May 1, 2000.

Zheng, Yingcong, etal.: "Identification of two novel *Drosophila melanogaster* histamine-gated chloride channel subunits expressed in the eye" Journal of Biological Chemistry, vol. 277, No. 3, Jan. 18, 2002, pp. 2000-2005.

Gengs, Chaoxian, etal.: "The target of *Drosophila* photoreceptor synaptic transmission is a histamine-gated chloride channel encoded by ort (hc1A)." Journal of Biological Chemistry, vol. 277, No. 44, Nov. 1, 2002, pp. 42113-42120.

Semenov, Eugene P., etal.: "Diversification of *Drosophila* chloride channel gene by multiple posttranscriptional mRNA modifications" Journal of Neurochemistry, vol. 72, No. 1, Jan. 1999, pp. 66-722.

* cited by examiner

```
1    CAATCGTCGC GATAACTCTG CCGTTTCTTT ATTGGTTTTT GCTGCGCGAC
51   GAGTAAAATA TAATTCCTCG CTTACTAATC CTCCGAGCAA GTTCATTCTC
101  AAGCGCACCC AGAGATGAGC TACTTTGGGA ATTGACATGG ACTGCGGAGC
151  AATGAGTGCC AGAGGAACAA TATCAAAGCC GAAGGTAGTG TGTTCATAAT
201  GCAAAGCCCA ACTAGCAAAT TGGTAGAATT CAGGTGCCTT ATTGCGTTGG
251  CAATATATTT GCACGCGCTG GAGCAATCGA TCCAGCACTG CCATTGTGTT
301  CATGGTTACA GAAATAACAC GGAGAGCGCC GAGCTGGTCT CCCACTACGA
351  GTCGAGTCTT TCGCTCCCGG ACATTTTGCC CATTCCCTCA AAGACGTACG
401  ACAAGAACCG GGCTCCCAAG CTCCTCGGCC AGCCCACAGT AGTCTACTTC
451  CATGTCACGG TCCTCTCCCT GGACTCCATT AACGAGGAGT CTATGACCTA
501  TGTGACGGAC ATCTTCCTTG CACAAAGCTG GCGTGATCCT CGCCTGCGGT
551  TGCCTGAGAA CATGAGTGAG CAGTATCGCA TATTGGATGT CGACTGGTTG
601  CACAGCATTT GGCGGCCCGA TTGCTTCTTT AAGAACGCCA AAAAGGTCAC
651  CTTCCATGAG ATGAGCATTC CCAATCACTA TCTCTGGCTG TACCACGACA
701  AAACGCTGCT CTATATGTCC AAACTCACGT TGGTCCTGTC GTGCGCCATG
751  AAGTTTGAGT CCTATCCGCA TGACACGCAA ATCTGCTCCA TGATGATCGA
801  GAGTTTATCC CATACGGTGG AAGATTTGGT TTTCATTTGG AACATGACCG
851  ACCCACTTGT GGTTAACACG GAGATTGAGT TGCCGCAGCT AGACATATCA
901  AATAACTACA CAACCGACTG TACTATAGAG TACTCAACAG GTAACTTCAC
951  CTGCCTGGCC ATTGTGTTCA ACCTGCGCCG ACGCCTGGGT TACCATTTGT
1001 TCCACACCTA CATCCCCTCG GCTCTGATTG TGGTCATGTC TTGGATATCG
1051 TTTTGGATAA AACCAGAAGC GATACCCGCC CGTGTAACTC TGGGAGTGAC
1101 CTCACTGCTA ACCCTGGCCA CCCAGAATAC CCAGTCGCAA CAATCGCTGC
1151 CGCCGGTTTC GTATGTCAAG GCTATAGACG TCTGGATGTC GTCCTGTTCG
1201 GTGTTTGTAT TCCTTTCTCT GATGGAATTT GCAGTGGTCA ACAATTTTAT
1251 GGGACCGGTG GCCACAAAGG CAATGAAGGG GTATTCGGAC GAGAACATCA
1301 GTGATCTGGA CGACCTAAAG TCTGCACTAC AGCATCATCG GGAATCGATT
1351 ATTGAGCCCC AGTACGACAC TTTCTGCCAT GGCCATGCCA CAGCCATTTA
1401 TATAGACAAA TTCTCGCGCT TTTTCTTCCC GTTTTCGTTC TTTATACTCA
1451 ATATTGTCTA TTGGACAACG TTCCTATGAT GGATGGAAAA GTTTCTCCGA
1501 AGGAATAGAG CGTAAACA (SEQ ID NO:1).
```

FIG. 1

```
1    MQSPTSKLVE  FRCLIALAIY  LHALEQSIQH  CHCVHGYRNN  TESAELVSHY
51   ESSLSLPDIL  PIPSKTYDKN  RAPKLLGQPT  VVYFHVTVLS  LDSINEESMT
101  YVTDIFLAQS  WRDPRLRLPE  NMSEQYRILD  VDWLHSIWRP  DCFFKNAKKV
151  TFHEMSIPNH  YLWLYHDKTL  LYMSKLTLVL  SCAMKFESYP  HDTQICSMMI
201  ESLSHTVEDL  VFIWNMTDPL  VVNTEIELPQ  LDISNNYTTD  CTIEYSTGNF
251  TCLAIVFNLR  RRLGYHLFHT  YIPSALIVVM  SWISFWIKPE  AIPARVTLGV
301  TSLLTLATQN  TQSQQSLPPV  SYVKAIDVWM  SSCSVFVFLS  LMEFAVVNNF
351  MGPVATKAMK  GYSDENISDL  DDLKSALQHH  RESIIEPQYD  TFCHGHATAI
401  YIDKFSRFFF  PFSFFILNIV  YWTTFL*  (SEQ ID NO:2).
```

FIG.2

```
1    CAATCGTCGC GATAACTCTG CCGTTTCTTT ATTGGTTTTT GCTGCGCGAC
51   GAGTAAAATA TAATTCCTCG CTTACTAATC CTCCGAGCAA GTTCATTCTC
101  AAGCGCACCC AGAGATGAGC TACTTTGGGA ATTGACATGG ACTGCGGAGC
151  AATGAGTGCC AGAGGAACAA TATCAAAGCC GAAGGTAGTG TGTTCATAAT
201  GCAAAGCCCA ACTAGCAAAT TGGTAGAATT CAGGTGCCTT ATTGCGTTGG
251  CAATATATTT GCACGCGCTG GAGCAATCGA TCCAGCACTG CCATTGTGTT
301  CATGGTTACA GAAATAACAC GGAGAGCGCC GAGCTGGTCT CCCACTACGA
351  GTCGAGTCTT TCGCTCCCGG ACATTTTGCC CATTCCCTCA AAGACGTACG
401  ACAAGAACCG GGCTCCCAAG CTCCTCGGCC AGCCCACAGT AGTCTACTTC
451  CATGTCACGG TCCTCTCCCT GGACTCCATT AACGAGGAGT CTATGACCTA
501  TGTGACGGAC ATCTTCCTTG CACAAAGCTG GCGTGATCCT CGCCTGCGGT
551  TGCCTGAGAA CATGAGTGAG CAGTATCGCA TATTGGATGT CGACTGGTTG
601  CACAGCATTT GGCGGCCCGA TTGCTTCTTT AAGAACGCCA AAAAGGTCAC
651  CTTCCATGAG ATGAGCATTC CCAATCACTA TCTCTGGCTG TACCACGACA
701  AAACGCTGCT CTATATGTCC AAACTCACGT TGGTCCTGTC GTGCGCCATG
751  AAGTTTGAGT CCTATCCGCA TGACACGCAA ATCTGCTCCA TGATGATCGA
801  GAGTTTATCC CATACGGTGG AAGATTTGGT TTTCATTTGG AACATGACCG
851  ACCCACTTGT GGTTAACACG GAGATTGAGT TGCCGCAGCT AGACATATCA
901  AATAACTACA CAACCGACTG TACTATAGAG TACTCAACAG GTAACTTCAC
951  CTGCCTGGCC ATTGTGTTCA ACCTGCGCCG ACGCCTGGGT TACCATTTGT
1001 TCCACACCTA CATCCCCTCG GCTCTGATTG TGGTCATGTC TTGGATATCG
1051 TTTTGGATAA AACCAGAAGC GATACCCGCC CGTGTAACTC TGGGAGTGAC
1101 CTCACTGCTA ACCCTGGCCA CCCAGAATAC CCAGTCGCAA CAATCGCTGC
1151 CGCCGGTTTC GTATGTCAAG GCTATAGACG TCTGGATGTC GTCCTGTTCG
1201 GTGTTTGTAT TCCTTTCTCT GATGGAATTT GCAGTGGTCA ACAATTTTAT
1251 GGGACCGGTG GCCACAAAGG CAATGAAGGG GTATTCGGAC GAGAACATCA
1301 GTGATCTGGA CGACCTAAAG CATCATCGGG AATCGATTAT TGAGCCCCAG
1351 TACGACACTT TCTGCCATGG CCATGCCACA GCCATTTATA TAGACAAATT
1401 CTCGCGCTTT TTCTTCCCGT TTTCGTTCTT TATACTCAAT ATTGTCTATT
1451 GGACAACGTT CCTATGATGG ATGGAAAAGT TTCTCCGAAG GAATAGAGCG
1501 TAAACA (SEQ ID NO:3).
```

FIG.3

```
1    MQSPTSKLVE  FRCLIALAIY  LHALEQSIQH  CHCVHGYRNN  TESAELVSHY
51   ESSLSLPDIL  PIPSKTYDKN  RAPKLLGQPT  VVYFHVTVLS  LDSINEESMT
101  YVTDIFLAQS  WRDPRLRLPE  NMSEQYRILD  VDWLHSIWRP  DCFFKNAKKV
151  TFHEMSIPNH  YLWLYHDKTL  LYMSKLTLVL  SCAMKFESYP  HDTQICSMMI
201  ESLSHTVEDL  VFIWNMTDPL  VVNTEIELPQ  LDISNNYTTD  CTIEYSTGNF
251  TCLAIVFNLR  RRLGYHLFHT  YIPSALIVVM  SWISFWIKPE  AIPARVTLGV
301  TSLLTLATQN  TQSQQSLPPV  SYVKAIDVWM  SSCSVFVFLS  LMEFAVVNNF
351  MGPVATKAMK  GYSDENISDL  DDLKHHRESI  IEPQYDTFCH  GHATAIYIDK
401  FSRFFFPFSF  FILNIVYWTT  FL* (SEQ ID NO:4).
```

FIG.4

AC15-4
AACTGCCAAG ACGTTTAGAA CGGAAAAACT GAATTTTCAA AAATATTTCG AGTAAACTGT
TAAATGCTGA AGTGTTCTGA AATATTCCTT AAAACATAGA AACCTTCTTT GACATCTTTA
TAAAGCAATA AAATTCATTC GGGAAGTTTA TGAATAGTGG TGTTATTAAT CATGCCATTT
GTGGCGTCAA GCTGATGGTT ATGTAATCTC TGTGAAGATT CTAGAAATCC AACAGAAATA
TATTGCTTCG AAAACCAAGC AAAGATTACT TGACTGGAGA GGAAAGCTAT TTCGAATTCA
TCTAAAAACT GTAAAGAGTT CACATTAAAA TGGTGTTCCA AATAATAATC CTGGTGATCT
GCACCATCTG CATGAAGCAC TACGCCAAAG GGGAGTTTCA ACAAAGTCTG GCCATAACCG
ACATCCTGCC CGAGGACATC AAGCGTTACG ACAAGATGAG ACCGCCGAAG AAAGAGGGTC
AGCCGACGAT AGTCTACTTC CATGTGACTG TGATGGGTCT GGACTCCATT GATGAGAACT
CGATGACTTA TGTGGCGGAT GTGTTCTTTG CACAGACGTG GAAGGATCAT CGCCTGCGAT
TGCCGGAGAA TATGACACAG GAATACCGCC TGCTCGAGGT GGACTGGCTA AAAAATATGT
GGCGCCCGGA TTCGTTTTTC AAAAACGCCA AATCGGTGAC CTTTCAGACC ATGACAATAC
CCAATCACTA TATGTGGCTG TACAAGGATA AGACCATTCT CTATATGGTC AAGCTAACAC
TGAAGCTGTC CTGCATCATG AATTTCGCCA TTTATCCTCA TGACACACAG GAGTGCAAGC
TGCAAATGGA AAGCCTGTCC CACACCACGG ATGACTTGAT ATTCCAGTGG GATCCAACAA
CGCCCCTTGT GGTTGATGAA AACATCGAAC TGCCGCAGGT GGCCCTCATC CGGAATGAAA
CGGCGGACTG CACCCAGGTT TATTCCACTG GCAACTTCAC ATGCCTGGAG GTGGTGTTCA
CCCTTAAGCG TCGTTTGGTT TACTACGTTT TCAACACCTA CATTCCCACC TGCATGATAG
TGATCATGTC ATGGGTATCC TTCTGGATCA AACCGGAGGC GGCACCAGCC CGTGTGACTC
TGGGTGTCAC CTCCTTGCTA ACGCTTTCCA CGCAACACGC CAAATCGCAG TCGTCTTTGC
CACCTGTTTC CTATCTCAAG GCAGTGGACG CCTTTATGTC CGTTTGCACG GTGTTCGTGT
TTATGGCCCT CATGGAGTAT TGTCTAATAA ACATCGTCCT GAGCGACACG CCCATTCCCA
AGCCGATGGC TTATCCACCC AAACCTGTGG CGGGCGATGG GCCCAAGAAA GAGGGCGAGG
GTGCTCCTCC TGGGGGCAGC AACTCGACGG CCAGCAAGCA ACAAGCCACC ATGTTGCCAC
TGGCCGATGA AAAGATCGAG AAAATTGAGA AGATCTTTGA CGAGATGACC AAGAATAGAA
GGATTGTAAC CACCACACGC CGCGTGGTGC GTCCACCATT GGACGCCGAT GGTCCGTGGA
TTCCGCGACA GGAGTCGCGG ATAATACTGA CCCCGACTAT CGCTCCGCCG CCACCGCCCC
CTCAGCCAGC GGCACCGGAA CCGGAACTAC CCAAGCCGAA ACTCACACCC GCCCAGGAGC
GGCTCAAGCG GCTATATAT ATAGATCGGT CCTCGCGCGT CCTTTTCCCC GCCCTCTTCG
CCAGTCTGAA TGGCATCTAC TGGTGTGTGT CTACGAGTA TCTATAAGGA CTACGACGAC
TGTGCCCTGT AAATACTTTC GCTAGCTCTC TGGCACTCCA TCCGAGTGTT AAACGTTGAT
TGTTCGCATA TATCGAAACG TGTATCGCAA ATTTAATCTT AAGCTTTCAC GCACAAGCTT
TAAGTCAATG AATTTTAAAC ATAGATTATT GTTAAACCAG AAGGAAGGAA TAATGGTACA
GATGGAGATC TGATTACAGG ATAAATTACA AATTATCAAT TCAATTCCTA AAATGCTTAA
AGTTAATCAA GTGACGTAGT AGCTGATGTA GCC (SEQ ID NO:5)

CGAGTAAACT GTTAAATGCT GAAGTGTTCT GAAATATTCC TTAAAACATA GAAACCTTCT
TTGACATCTT TATAAAGCAA TAAAATTCAT TCGGGAAGTT TATGAATAGT GGTGTTATTA
ATCATGCCAT TTGTGGCGTC AAGCTGATGG TTATGTAATC TCTGTGAAGA TTCTAGAAAT
CCAACAGAAA TATATTGCTT CGAAAACCAA GCAAAGATTA CTTGACTGGA GAGGAAAGCT
ATTTCGAATT CATCTAAAAA CTGTAGCTCA CATTAAAATG GTGTTCCAAA TAATAATCCT
GGTGATCTGC ACCATCTGCA TGAAGCACTA CGCCAAAGGG GAGTTTCAAC AAAGTCTGGC
CATAACCGAC ATCCTGCCCG AGGACATCAA GCGTTACGAC AAGATGAGAC CGCCGAAGAA
AGAGGGTCAG CCGACGATAG TCTACTTCCA TGTGACTGTG ATGGGTCTGG ACTCCATTGA
TGAGAACTCG ATGACTTATG TGGCGGATGT GTTCTTTGCA CAGACGTGGA AGGATCATCG
CCTGCGATTG CCGGAGAATA TGACACAGGA ATACCGCCTG CTCGAGGTGG ACTGGCTAAA
AAATATGTGG CGGCCGGATT CGTTTTTCAA AAACGCCAAA TCGGTGACCT TTCAGACCAT
GACAATACCC AATCACTATA TGTGGCTGTA CAAGGATAAG ACCATTCTGT ACATGGTCAA
ACTAACACTG AAGCTGTCCT GCATCATGAA CTTCGCCATT TATCCTCATG ATACACAGGA
GTGCAAGCTG CAAATGGAAA GCCTGTCCCA CACCACGGAT GACTTGATAT TTCAGTGGGA
TCCAACGACG CCCCTTGTGG TTGATGAAAA CATCGAGCTG CCGCAGGTGG CCCTCATCCG
AAATGAAACG GCGGACTGTA CCCAAGTTTA TTCCACTGGC AACTTCACAT GCCTGGAGGT
GGTGTTCACC CTTAAGCGTC GTTTGGTTTA CTACGTTTTC AACACCTACA TTCCCACCTG
CATGATAGTG ATCATGTCAT GGGTATCCTT CTGGATCAAA CCGGAGGCGG CACCAGCCCG
TGTGACTCTG GGTGTCACCT CCTTGCTAAC GCTTTCCACG CAACACGCCA AATCGCAGTC
GTCTTTGCCA CCTGTTTCCT ATCTCAAGGC AGTGGACGCC TTTATGTCCG TTTGCACGGT
GTTCGTGTTT ATGGCCCTCA TGGAGTATTG TCTAATAAAC ATCGTCCTGA GCGACACGCC
CATTCCCAAG CCGATGGCCT ATCCACCCAA ACCTGTGGCG GGAGATGGGC CAAGAAAGA
GGGCGAGGGT GCTCCTCCTG GGGGCAGCAA CTCGACGGCC AGCAAGCAAC AAGCCACCAT
GTTGCCACTG GCCGATGAAA AGATCGAGAA AATTGAGAAG ATCTTTGACG AGATGACCAA
GAATAGAAGG ATTGTAACCA CCACACGCCG CGTGGTGCGT CCGCCATTGG ACGCCGATGG
TCCGTGGATT CCGCGACAGG AGTCGCGGAT AATACTGACC CCGACTATCG CTCCGCCGCC
ACCGCCCCCT CAGCCAGCGG CACCGGAACC GGAACTGCCC AAGCCGAAAC TCACACCCGC
CCAGGAGCGG CTCAAGCGGG CTATATATAT AGATCGGTCC TCGCGCGTCC TTTTCCCCGC
CCTCTTCGCC AGTCTGAATG GCATCTACTG GTGTGTGTTC TACGAGTATC TATAAGGACT
ACGACGACTG TGCCCTGTAA ATACTTTCGC TAGCTCTCTG GCACTCCATC CGAGTGTTAA
ACGTTGATTG TTCGCATATA TCGAAACGTG TATCGCAAAT TTAATCTTAA GCTTTCACGC
ACAAGCTTTA AGTCAATGAA TTTTAAACAT AGATTATTGT TAAACCAGAA GGAAGGAATA
ATGGTACAGA TGGAGATCTG ATTACAGGAT AAAATTACAAA TTATCAATTC AATTCCTAAA
ATGCTTAAAG TTAATCAAGT GACGTAGTAG CTGATGTAGC CTAAGTGAAT TGTA (SEQ ID
NO:6).

FIG.6

```
MVFQIIILVI CTICMKHYAK GEFQQSLAIT DILPEDIKRY DKMRPPKKEG
QPTIVYFHVT VMGLDSIDEN SMTYVADVFF AQTWKDHRLR LPENMTQEYR
LLEVDWLKNM WRPDSFFKNA KSVTFQTMTI PNHYMWLYKD KTILYMVKLT
LKLSCIMNFA IYPHDTQECK LQMESLSHTT DDLIFQWDPT TPLVVDENIE
LPQVALIRNE TADCTQVYST GNFTCLEVVF TLKRRLVYYV FNTYIPTCMI
VIMSWVSFWI KPEAAPARVT LGVTSLLTLS TQHAKSQSSL PPVSYLKAVD
AFMSVCTVFV FMALMEYCLI NIVLSDTPIP KPMAYPPKPV AGDGPKKEGE
GAPPGGSNST ASKQQATMLP LADEKIEKIE KIFDEMTKNR RIVTTTRRVV
RPPLDADGPW IPRQESRIIL TPTIAPPPPP PQPAAPEPEL PKPKLTPAQE
RLKRAIYIDR SSRVLFPALF ASLNGIYWCV FYEYL* (SEQ ID NO:7).
```

FIG. 7

DNA MOLECULES ENCODING LIGAND-GATED ION CHANNELS FROM DROSOPHILA MELANOGASTER

CROSS-REFERENCE TO RELATED APPLICATIONS

This application is the §371 National Stage prosecution of PCT International Application serial no. PCT/US01/06096, having an international filing date of Feb. 26, 2001, which claims the benefit under 35 U.S.C. §119(e) to U.S. Provisional Application Ser. No. 60/186,645, filed Mar. 2, 2000, now expired.

STATEMENT REGARDING FEDERALLY-SPONSORED R&D

Not Applicable

REFERENCE TO MICROFICHE APPENDIX

Not Applicable

FIELD OF THE INVENTION

The present invention relates in part to isolated nucleic acid molecules (polynucleotides) which encode *Drosophila melanogaster* ligand-gated ion channels. The present invention also relates to recombinant vectors and recombinant hosts which contain a DNA fragment encoding *Drosophila* ligand-gated ion channels, substantially purified forms of associated *Drosophila* ligand-gated ion channels and recombinant membrane fractions comprising these proteins, associated mutant proteins, and methods associated with identifying compounds which modulate associated *Drosophila melanogaster* ligand-gated ion channels, which will be useful as insecticides.

BACKGROUND OF THE INVENTION

Glutamate-gated chloride channels, or H-receptors, have been identified in arthropod nerve and muscle (Lingle et al, 1981, *Brain Res.* 212: 481–488; Horseman et al., 1988, *Neurosci. Lett.* 85: 65–70; Wafford and Sattelle, 1989, *J. Exp. Bio.* 144: 449–462; Lea and Usherwood, 1973, *Comp. Gen. Parmacol.* 4: 333–350; and Cull-Candy, 1976, *J. Physiol.* 255: 449–464).

Invertebrate glutamate-gated chloride channels are important targets for the widely used avermectin class of anthelmintic and insecticidal compounds. The avermectins are a family of macrocyclic lactones originally isolated from the actinomycete *Streptomyces avermitilis*. The semisynthetic avermectin derivative, ivermectin (22,23-dihydro-avermectin $B_{1a}$), is used throughout the world to treat parasitic helminths and insect pests of man and animals. The avermectins remain the most potent broad spectrum endectocides exhibiting low toxicity to the host. After many years of use in the field, there remains little resistance to avermectin in the insect population. The combination of good therapeutic index and low resistance strongly suggests that the glutamate-gated chloride (GluCl) channels remain good targets for insecticide development.

Glutamate-gated chloride channels have been cloned from the soil nematode *Caenorhabditis elegans* (Cully et al., 1994, *Nature* 371: 707–711; see also U.S. Pat. No. 5,527,703 and Arena et al., 1992, *Molecular Brain Research*. 15: 339–348) and *Ctenocephalides felis* (flea; see WO 99/07828).

In addition, a gene encoding a glutamate-gated chloride channel from *Drosophila melanogaster* was previously identified (Cully et al., 1996, *J. Biol. Chem.* 271: 20187–20191; see also U.S. Pat. No.5,693,492).

O'Tousa et al. (1989, *J. Neurogenetics* 6: 41–52) map photoreceptor mutations to the ChIII 92B region of the *Droshphila* genome.

Stuart, 1999, *Neuron* 22:431–433 reviews the art which suggests that histamine is an invertrbrate nuerotransmitter.

Despite the identification of the aforementioned cDNA clones encoding GluCls, including a previous identification of a *Drosophila* GluCl gene (see U.S. Pat. No. 5,693,492), it would be advantageous to identify additional genes which encode invertebrate ligand-gated ion channels, including but not limited to additional GluCls or other ligand-gated channels, such as a ligand-gated ion channel (LGIC) which is activated by histamine, which may provide additional targets for effective insecticides, in turn allowing for improved screening to identify novel LGIC modulators that may have insecticidal, mitacidal and/or nematocidal activity for animal health or crop protection. The present invention addresses and meets these needs by disclosing novel genes which express a *Drosophila melanogaster* ligand-gated ion channel, wherein expression of the respective *Drosophila* gene in *Xenopus* oocytes or other appropriate host cell results in an active LGIC. Heterologous expression of a respective LGIC(s) of the present invention will allow the pharmacological analysis of compounds active against parasitic invertebrate species relevant to animal and human health. Such species include worms, fleas, tick, and lice. Heterologous cell lines expressing an active LGIC can be used to establish functional or binding assays to identify novel LGIC modulators that may be useful in control of the aforementioned species groups.

SUMMARY OF THE INVENTION

The present invention relates to an isolated or purified nucleic acid molecule (polynucleotide) which encodes a novel *Drosophila melanogaster* invertebrate ligand-gated ion channel (LGIC) protein which comprises at least a portion of a LGIC receptor. The DNA molecules disclosed herein may be transfected into a host cell of choice wherein the recombinant host cell provides a source for substantial levels of an expressed functional single, homomultimer or heteromultimer LGIC channel. The cDNA clones described herein express a functional single channel protein, both of which are activated by histamine. Therefore, these DmLGIC channels form receptors which provide for additional screening targets to identify modulators of these channels, modulators which may act as effective insecticidal, mitacidal and/or nematocidal treatment for use in animal and human health and/or crop protection.

The present invention further relates to an isolated nucleic acid molecule (polynucleotide) which encodes mRNA which expresses a novel *Drosophila melanogaster* LGIC protein, this DNA molecule comprising the nucleotide sequence disclosed herein as SEQ ID NO:1, SEQ ID NO:3, SEQ ID NO:5 and SEQ ID NO:6.

The present invention also relates to biologically active fragments or mutants of SEQ ID NOs: 1, 3, 5 and 6 which encode mRNA expressing a novel *Drosophila melanogaster* invertebrate LGIC protein. Any such biologically active fragment and/or mutant will encode either a protein or protein fragment which at least substantially mimics the pharmacological properties of the respective *Drosophila* LGIC protein, including but not limited to the *Drosophila*

LGIC proteins as set forth in SEQ ID NO:2, SEQ ID NO:4, and SEQ ID NO:7. Any such polynucleotide includes but is not necessarily limited to nucleotide substitutions, deletions, additions, amino-terminal truncations and carboxy-terminal truncations such that these mutations encode mRNA which express a functional *Drosophila* LGIC in a eukaryotic cell, such as *Xenopus* oocytes, so as to be useful for screening for agonists and/or antagonists of *Drosophila* LGIC activity.

A preferred aspect of this portion of the present invention is disclosed in FIG. 1 (SEQ ID NO:1; designated AC05-10), FIG. 3 (SEQ ID NO:3; designated AC05-11), FIG. 5 (SEQ ID NO:5; designated AC15-4) and FIG. 6 (SEQ ID NO:6) encoding a novel *Drosophila melanogaster* LGIC protein.

The isolated nucleic acid molecules of the present invention may include a deoxyribonucleic acid molecule DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant host cells, both prokaryotic and eukaryotic, which contain the nucleic acid molecules disclosed throughout this specification.

The present invention also relates to a substantially purified form of a *Drosophila* LGIC protein, which comprises the amino acid sequence disclosed in FIG. 2 (SEQ ID NO:2), FIG. 4 (SEQ ID NO:4) and FIG. 7 (SEQ ID NO:7).

A preferred aspect of this portion of the present invention is a *Drosophila* LGIC protein which consists of the amino acid sequence disclosed in FIG. 2 (SEQ ID NO:2), FIG. 4 (SEQ ID NO:4) and FIG. 7 (SEQ ID NO:7).

Another preferred aspect of the present invention relates to a substantially purified, fully processed (including proteolytic processing, glycosylation and/or phosphorylation), mature LGIC protein obtained from a recombinant host cell containing a DNA expression vector comprising nucleotide sequence as set forth in SEQ ID NOs: 1, 3, 5 and/or 6 which express the respective DmLGIC protein. It is especially preferred is that the recombinant host cell be a eukaryotic host cell, such as a mammalian cell line, or *Xenopus* oocytes, as noted above.

Another preferred aspect of the present invention relates to a substantially purified membrane preparation, partially purified membrane preparation, or cell lysate which has been obtained from a recombinant host cell transformed or transfected with a DNA expression vector which comprises and appropriately expresses a complete open reading frame as set forth in SEQ ID NOs: 1, 3, 5 and/or 6, resulting in a functional form of the respective DmLGIC. The subcellular membrane fractions and/or membrane-containing cell lysates from the recombinant host cells (both prokaryotic and eukaryotic as well as both stably and transiently transformed cells) contain the functional and processed proteins encoded by the nucleic acids of the present invention. This recombinant-based membrane preparation may comprise a *Drosophila* LGIC and is essentially free from contaminating proteins, including but not limited to other *Drosophila* source proteins or host proteins from a recombinant cell which expresses the AC05-10 (SEQ ID NO:2), AC05-11 (SEQ ID NO:4) and/or AC154/AC15-25 (SEQ ID NO:7) LGIC protein. Therefore, a preferred aspect of the invention is a membrane preparation which contains a *Drosophila* LGIC comprising the functional form of the full length LGIC proteins as disclosed in FIG. 2 (SEQ ID NO:2, AC05-10), FIG. 4 (SEQ ID NO:4, AC05-11), and FIG. 7 (SEQ ID NO:7, AC15-4/AC14-25). These subcellular membrane fractions will comprise either wild type and/or mutant variations which are biologically functional forms of the *Drosophila* LGIC (including but not limited to functional channels generated by a single polypeptide, or any homomultimer or heteromultimer channel combinations thereof) at levels substantially above endogenous levels. Any such channel will be useful in various assays described throughout this specification to select for modulators of the respective LGIC channel. A preferred eukaryotic host cell of choice to express the LGICs of the present invention is a mammalian cell line, or *Xenopus* oocytes.

The present invention also relates to biologically active fragments and/or mutants of an *Drosophila* LGIC protein, comprising the amino acid sequence as set forth in SEQ ID NOs: 2, 4 and/or 7, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for selective modulators, including but not limited to agonists and/or antagonists for *Drosophila* ligand-gated ion channel pharmacology.

A preferred aspect of the present invention is disclosed in FIG. 2 (SEQ ID NO:2), FIG. 4 (SEQ ID NO:4) and FIG. 7 (SEQ ID NO:7), respective amino acid sequences which compose the *Drosophila* LGIC proteins of the present invention. Characterization of one or more of these channel proteins allows for screening to identify novel LGIC modulators that may have insecticidal, mitacidal and/or nematocidal activity for animal health or crop protection. As noted above, heterologous expression of functional single channel, homomultimer and/or heteromultimer combination of *Drosophila melanogaster* LGICs disclosed herein is contemplated at levels substantially above endogenous levels and will allow for the pharmacological analysis of compounds active against parasitic invertebrate species relevant to animal and human health. Such species include worms, fleas, tick, and lice. Heterologous cell lines expressing a functional DmLGIC channel (e.g., functional forms of SEQ ID NOs: 2, 4 and/or 7), can be used to establish functional or binding assays to identify novel LGIC modulators that may be useful in control of the aforementioned species groups.

The present invention also relates to polyclonal and monoclonal antibodies raised against forms of DmLGIC, or a biologically active fragment thereof.

The present invention also relates to DmLGIC fusion constructs, including but not limited to fusion constructs which express a portion of the DmLGIC linked to various markers, including but in no way limited to GFP (Green fluorescent protein), the MYC epitope, GST, and Fc. Any such fusion constructs may be expressed in the cell line of interest and used to screen for modulators of one or more of the DmLGIC proteins disclosed herein.

The present invention relates to methods of expressing *Drosophila* LGIC proteins and biological equivalents disclosed herein, assays employing these gene products, recombinant host cells which comprise DNA constructs which express these proteins, and compounds identified through these assays which act as agonists or antagonists of LGIC activity.

It is an object of the present invention to provide an isolated nucleic acid molecule (e.g., SEQ ID NOs: 1, 3, 5 and 6) which encodes a novel form of *Drosophila* LGIC, or fragments, mutants or derivatives DmLGIC, as set forth in SEQ ID NOs: 2, 4, and 7, respectively. Any such polynucleotide includes but is not necessarily limited to nucleotide substitutions, deletions, additions, amino-terminal truncations and carboxy-terminal truncations such that these mutations encode MRNA which express a protein or protein fragment of diagnostic, therapeutic or prophylactic use and would be useful for screening for selective modulators for invertebrate ligand-gated ion channel pharmacology.

It is a further object of the present invention to provide the *Drosophila* LGIC proteins or protein fragments encoded by the nucleic acid molecules referred to in the preceding paragraph.

It is a further object of the present invention to provide recombinant vectors and recombinant host cells which comprise a nucleic acid sequence encoding *Drosophila* LGIC proteins or a biological equivalent thereof.

It is an object of the present invention to provide a substantially purified form of *Drosophila* LGIC proteins, as set forth in SEQ ID NOs: 2, 4, and 7.

Is another object of the present invention to provide a substantially purified recombinant form of a *Drosophila* LGIC protein which has been obtained from a recombinant host cell transformed or transfected with a DNA expression vector which comprises and appropriately expresses a complete open reading frame as set forth in SEQ ID NOs: 1, 3, 5 and 6, resulting in a functional, processed form of the respective DmLGIC. It is especially preferred is that the recombinant host cell be a eukaryotic host cell, such as a mammalian cell line.

It is an object of the present invention to provide for biologically active fragments and/or mutants of *Drosophila* LGIC proteins, such as set forth in SEQ ID NOs: 2, 4, and 7, including but not necessarily limited to amino acid substitutions, deletions, additions, amino terminal truncations and carboxy-terminal truncations such that these mutations provide for proteins or protein fragments of diagnostic, therapeutic and/or prophylactic use.

It is further an object of the present invention to provide for substantially purified subcellular membrane preparations, partially purified subcellular membrane preparations, or crude lysates from recombinant cells which comprise pharmacologically active *Drosophila* LGICs, especially subcellular fractions obtained from a host cell transfected or transformed with a DNA vector comprising a nucleotide sequence which encodes a protein which comprises the amino acid as set forth in FIG. 2 (SEQ ID NO:2), FIG. 4 (SEQ ID NO:4) and/or FIG. 7 (SEQ ID NO:7).

It is another object of the present invention to provide a substantially purified membrane preparation, partially purified subcellular membrane preparations, and/or crude lysates obtained from a recombinant host cell transformed or transfected with a DNA expression vector which comprises and appropriately expresses a complete open reading frame as set forth in SEQ ID NOs: 1, 3, 5, and/or 6, resulting in a functional, processed form of the respective DmLGIC. It is especially preferred is that the recombinant host cell be a eukaryotic host cell, such as a mammalian cell line, or *Xenopus* oocytes.

It is also an object of the present invention to use *Drosophila* LGIC proteins or membrane preparations containing *Drosophila* LGIC proteins or a biological equivalent to screen for modulators, preferably selective modulators, of *Drosophila* LGIC activity. Any such protein or membrane associated protein may be useful in screening and selecting these modulators active against parasitic invertebrate species relevant to animal and human health. Such species include worms, fleas, tick, and lice. These membrane preparations may be generated from heterologous cell lines expressing these LGICs and may constitute full length protein, biologically active fragments of the full length protein or may rely on fusion proteins expressed from various fusion constructs which may be constructed with materials available in the art.

As used herein, "substantially free from other nucleic acids" means at least 90%, preferably 95%, more preferably 99%, and even more preferably 99.9%, free of other nucleic acids. As used interchangeably with the terms "substantially free from other nucleic acids" or "substantially purified" or "isolated nucleic acid" or "purified nucleic acid" also refer to a DNA molecules which comprises a coding region for a *Drosophila* LGIC protein that has been purified away from other cellular components. Thus, a *Drosophila* LGIC DNA preparation that is substantially free from other nucleic acids will contain, as a percent of its total nucleic acid, no more than 10%, preferably no more than 5%, more preferably no more than 1%, and even more preferably no more than 0.1%, of non-*Drosophila* LGIC nucleic acids. Whether a given *Drosophila* LGIC DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, a *Drosophila* LGIC protein preparation that is substantially free from other proteins will contain, as a percent of its total protein, no more than 10%, preferably no more than 5%, more preferably no more than 1%, and even more preferably no more than 0.1%, of non-*Drosophila* LGIC proteins. Whether a given *Drosophila* LGIC protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting. As used interchangeably with the terms "substantially free from other proteins" or "substantially purified", the terms "isolated *Drosophila* LGIC protein" or "purified *Drosophila* LGIC protein" also refer to *Drosophila* LGIC protein that has been isolated from a natural source. Use of the term "isolated" or "purified" indicates that *Drosophila* LGIC protein has been removed from its normal cellular environment. Thus, an isolated *Drosophila* LGIC protein may be in a cell-free solution or placed in a different cellular environment from that in which it occurs naturally. The term isolated does not imply that an isolated *Drosophila* LGIC protein is the only protein present, but instead means that an isolated *Drosophila* LGIC protein is substantially free of other proteins and non-amino acid material (e.g., nucleic acids, lipids, carbohydrates) naturally associated with the *Drosophila* LGIC protein in vivo. Thus, a *Drosophila* LGIC protein that is recombinantly expressed in a prokaryotic or eukaryotic cell and substantially purified from this host cell which does not naturally (i.e., without intervention) express this LGIC protein is of course "isolated *Drosophila* LGIC protein" under any circumstances referred to herein. As noted above, a *Drosophila* LGIC protein preparation that is an isolated or purified *Drosophila* LGIC protein will be substantially free from other proteins will contain, as a percent of its total protein, no more than 10%, preferably no more than 5%, more preferably no more than 1%, and even more preferably no more than 0. 1%, of non-*Drosophila* LGIC proteins.

As used interchangeably herein, "functional equivalent" or "biologically active equivalent" means a protein which does not have exactly the same amino acid sequence as naturally occurring *Drosophila* LGIC, due to alternative splicing, deletions, mutations, substitutions, or additions, but retains substantially the same biological activity as *Drosophila* LGIC. Such functional equivalents will have significant amino acid sequence identity with naturally occurring *Drosophila* LGIC and genes and cDNA encoding such functional equivalents can be detected by reduced stringency hybridization with a DNA sequence encoding naturally occurring *Drosophila* LGIC. For example, a naturally occurring *Drosophila* LGIC disclosed herein comprises the amino acid sequence shown as SEQ ID NO:2 and is encoded by SEQ ID NO: 1. A nucleic acid encoding a functional equivalent has at least about 50% identity at the nucleotide level to SEQ ID NO: 1.

As used herein, "a conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

As used herein, "LGIC" refers to a—ligand-gated ion channel—.

As used herein, "DmLGIC" refers to a—*Drosophila melanogaster* ligand-gated ion channel—.

As used herein, "GluCl" refers to—L-glutamate gated chloride channel—.

As used herein, "DmGluCl" refers to—*Drosophila melanogaster* L-glutamate gated chloride channel—.

As used herein, the term "mammalian" will refer to any mammal, including a human being.

BRIEF DESCRIPTION OF THE DRAWINGS

FIG. 1 shows the nucleotide sequence which of the *Drosophila* LGIC clone, AC05-10, as set forth in SEQ ID NO:1.

FIG. 2 shows the amino acid sequence of the *Drosophila* LGIC AC05-10 protein, as set forth in SEQ ID NO:2.

FIG. 3 shows the nucleotide sequence which of the *Drosophila* LGIC clone, AC05-11, as set forth in SEQ ID NO:3.

FIG. 4 shows the amino acid sequence of the *Drosophila* LGIC AC05-11 protein, as set forth in SEQ ID NO:4.

FIG. 5 shows the nucleotide sequence which of the *Drosophila* LGIC clone, AC154, as set forth in SEQ ID NO:5.

FIG. 6 shows the nucleotide sequence which of the *Drosophila* LGIC clone, AC15-25, as set forth in SEQ ID NO:6.

FIG. 7 shows the amino acid sequence of the *Drosophila* LGIC AC154/AC15-25 protein, as set forth in SEQ ID NO:7.

DETAILED DESCRIPTION OF THE INVENTION

Figure 8:
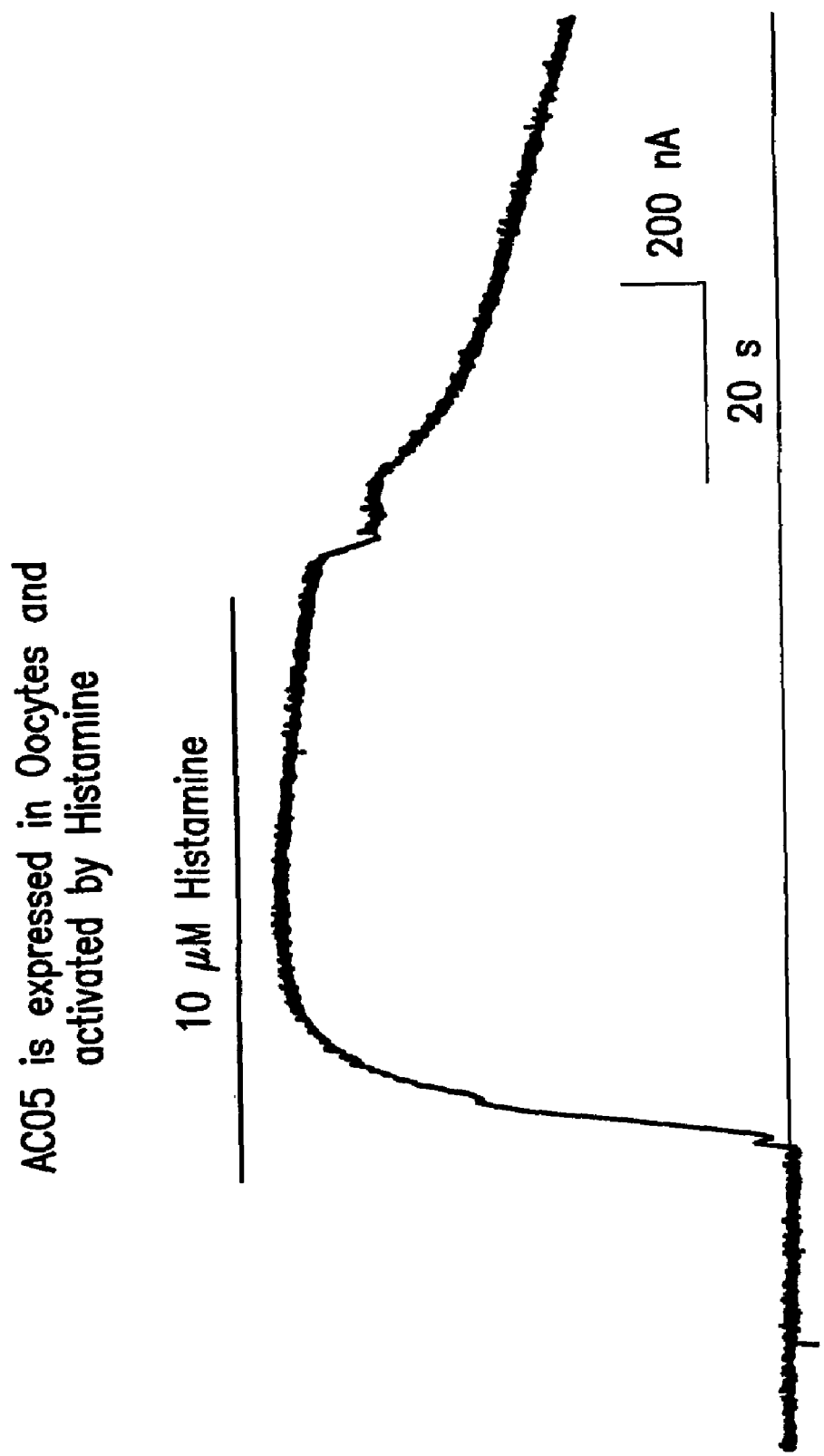
FIG. 8 shows the activation of a recombinant DmLGIC (AC05-10) by histamine in transfected *Xenopus* oocytes.

The present invention relates to an isolated nucleic acid molecule (polynucleotide) which encodes a *Drosophila melanogaster* invertebrate LGIC protein, which are phylogentically related to known DmGluCl proteins but which show alternative pharmacology, and hence, represent novel insecticide targets. The isolated or purified nucleic acid molecules of the present invention are substantially free from other nucleic acids. For most cloning purposes, DNA is a preferred nucleic acid. As noted above, the DNA molecules disclosed herein it may be transfected into a host cell of choice wherein the recombinant host cell provides a source for substantial levels of an expressed functional single, homomultimer or heteromultimer LGIC channel. The cDNA clones described herein express a functional single channel protein, both of which are activated by histamine. Therefore, these DmLGIC channels form receptors which provide for additional screening targets to identify modulators of these channels, modulators which may act as effective insecticidal, mitacidal and/or nematocidal treatment for use in animal and human health and/or crop protection. The DNA molecules disclosed herein are transfected into a host cell of choice wherein the recombinant host cell provides a source for substantial levels of an expressed functional single, homomultimer or heteromultimer LGIC channel.

The present invention relates to an isolated nucleic acid molecule (polynucleotide) which encodes mRNA which expresses a novel *Drosophila melanogaster* invertebrate LGIC protein, this DNA molecule comprising the nucleotide sequence disclosed herein as SEQ ID NO:1, SEQ ID NO:3, SEQ ID NO:5, and SEQ ID NO:6. The isolation and characterization of the DmLGIC nucleic acid molecules of the present invention were identified as described in detail in Example Section 1.

Invertebrate glutamate-gated chloride channels (GluCls) are related to the glycine- and GABA-gated chloride channels and are distinct from the excitatory glutamate receptors (e.g. NMDA or AMPA receptors). The first two members of the GluCl family were identified in the nematode *C. elegans,* following a functional screen for the receptor of the anthelmintic drug ivermectin. Several additional GluCls have now been cloned in other invertebrate species. However, there is no evidence yet for GluCl counterparts in vertebrates; because of this, GluCls and any related ligand-gated channels are potentially excellent targets for anthelmintics, insecticides, acaricides, etc. Specific GluCl modulators, such as nodulisporic acid and its derivatives, indeed have an ideal safety profile because they lack mechanism-based toxicity in vertebrates. The present invention relates in part to four novel *Drosophila* LGIC clones, AC05-10, AC05-11, AC154 and AC15-25, which show homology to the earlier identified DmGluClα and to *C. felis* CfGluCl DNA.

The present invention relates to the isolated or purified DNA molecule described in FIG. 1 (AC05-10) and set forth as SEQ ID NO:1, which encodes the *Drosophila* LGIC protein described in FIG. 2 and set forth as SEQ ID NO:2, the nucleotide sequence of AC05-10 is as follows:

CAATCGTCGC GATAACTCTG CCGTTTCTTT ATTGGTTTTT GCTGCGCGAC GAGTAAAATA (SEQ ID NO:1)

TAATTCCTCG CTTACTAATC CTCCGAGCAA GTTCATTCTC AAGCGCACCC AGAGATGAGC

```
TACTTTGGGA ATTGACATGG ACTGCGGAGC AATGAGTGCC AGAGGAACAA TATCAAAGCC

GAAGGTAGTG TGTTCATAAT GCAAAGCCCA ACTAGCAAAT TGGTAGAATT CAGGTGCCTT

ATTGCGTTGG CAATATATTT GCACGCGCTG GAGCAATCGA TCCAGCACTG CCATTGTGTT

CATGGTTACA GAAATAACAC GGAGAGCGCC GAGCTGGTCT CCCACTACGA GTCGAGTCTT

TCGCTCCCGG ACATTTTGCC CATTCCCTCA AAGACGTACG ACAAGAACCG GGCTCCCAAG

CTCCTCGGCC AGCCCACAGT AGTCTACTTC CATGTCACGG TCCTCTCCCT GGACTCCATT

AACGAGGAGT CTATGACCTA TGTGACGGAC ATCTTCCTTG CACAAAGCTG GCGTGATCCT

CGCCTGCGGT TGCCTGAGAA CATGAGTGAG CAGTATCGCA TATTGGATGT CGACTGGTTG

CACAGCATTT GGCGGCCCGA TTGCTTCTTT AAGAACGCCA AAAAGGTCAC CTTCCATGAG

ATGAGCATTC CAAGCACTA TCTCTGGCTG TACCACGACA AAACGCTGCT CTATATGTCC

AAACTCACGT TGGTCCTGTC GTGCGCCATG AAGTTTGAGT CCTATCCGCA TGACACGCAA

ATCTGCTCCA TGATGATCGA GAGTTTATCC CATACGGTGG AAGATTTGGT TTTCATTTGG

AACATGACCG ACCCACTTGT GGTTAACACG GAGATTGAGT TGCCGCAGCT AGACATATCA

AATAACTACA CAACCGACTG TACTATAGAG TACTCAACAG GTAACTTCAC CTGCCTGGCC

ATTGTGTTCA ACCTGCGCCG ACGCCTGGGT TACCATTTGT TCCACACCTA CATCCCCTCG

GCTCTGATTG TGGTCATGTC TTGGATATCG TTTTGGATAA AACCAGAAGC GATACCCGCC

CGTGTAACTC TGGGAGTGAC CTCACTGCTA ACCCTGGCCA CCCAGAATAC CCAGTCGCAA

CAATCGCTGC CGCCGGTTTC GTATGTCAAG GCTATAGACG TCTGGATGTC GTCCTGTTCG

GTGTTTGTAT TCCTTTCTCT GATGGAATTT GCAGTGGTCA ACAATTTTAT GGGACCGGTG

GCCACAAAGG CAATGAAGGG GTATTCGGAC GAGAACATCA GTGATCTGGA CGACCTAAAG

TCTGCACTAC AGCATCATCG GGAATCGATT ATTGAGCCCC AGTACGACAC TTTCTGCCAT

GGCCATGCCA CAGCCATTTA TATAGACAAA TTCTCGCGCT TTTTCTTCCC GTTTTCGTTC

TTTATACTCA ATATTGTCTA TTGGACAACG TTCCTATGAT GGATGGAAAA GTTTCTCCGA

AGGAATAGAG CGTAAACA.
```

The present invention also relates to the isolated or purified DNA molecule described in FIG. 3 (AC05-1 1) and set forth as SEQ ID NO:3, which encodes the *Drosophila* LGIC protein described in FIG. 4 and set forth as SEQ ID NO:4, the nucleotide sequence AC05-11 as follows:

```
CAATCGTCGC GATAACTCTG CCGTTTCTTT ATTGGTTTTT GCTGCGCGAC GAGTAAAATA    (SEQ ID NO:3)

TAATTCCTCG CTTACTAATC CTCCGAGCAA GTTCATTCTC AAGCGCACCC AGAGATGAGC

TACTTTGGGA ATTGACATGG ACTGCGGAGC AATGAGTGCC AGAGGAACAA TATCAAAGCC

GAAGGTAGTG TGTTCATAAT GCAAAGCCCA ACTAGCAAAT TGGTAGAATT CAGGTGCCTT

ATTGCGTTGG CAATATATTT GCACGCGCTG GAGCAATCGA TCCAGCACTG CCATTGTGTT

CATGGTTACA GAAATAACAC GGAGAGCGCC GAGCTGGTCT CCCACTACGA GTCGAGTCTT

TCGCTCCCGG ACATTTTGCC CATTCCCTCA AAGACGTACG ACAAGAACCG GGCTCCCAAG

CTCCTCGGCC AGCCCACAGT AGTCTACTTC CATGTCACGG TCCTCTCCCT GGACTCCATT

AACGAGGAGT CTATGACCTA TGTGACGGAC ATCTTCCTTG CACAAAGCTG GCGTGATCCT

CGCCTGCGGT TGCCTGAGAA CATGAGTGAG CAGTATCGCA TATTGGATGT CGACTGGTTG
```

-continued

```
CACAGCATTT GGCGGCCCGA TTGCTTCTTT AAGAACGCCA AAAAGGTCAC CTTCCATGAG

ATGAGCATTC CCAATCACTA TCTCTGGCTG TACCACGACA AAACGCTGCT CTATATGTCC

AAACTCACGT TGGTCCTGTC GTGCGCCATG AAGTTTGAGT CCTATCCGCA TGACACGCAA

ATCTGCTCCA TGATGATCGA GAGTTTATCC CATACGGTGG AAGATTTGGT TTTCATTTGG

AACATGACCG ACCCACTTGT GGTTAACACG GAGATTGAGT TGCCGCAGCT AGACATATCA

AATAACTACA CAACCGACTG TACTATAGAG TACTCAACAG GTAACTTCAC CTGCCTGGCC

ATTGTGTTCA ACCTGCGCCG ACGCCTGGGT TACCATTTGT TCCACACCTA CATCCCCTCG

GCTCTGATTG TGGTCATGTC TTGGATATCG TTTTGGATAA AACCAGAAGC GATACCCGCC

CGTGTAACTC TGGGAGTGAC CTCACTGCTA ACCCTGGCCA CCCAGAATAC CCAGTCGCAA

CAATCGCTGC CGCCGGTTTC GTATGTCAAG GCTATAGACG TCTGGATGTC GTCCTGTTCG

GTGTTTGTAT TCCTTTCTCT GATGGAATTT GCAGTGGTCA ACAATTTTAT GGGACCGGTG

GCCACAAAGG CAATGAAGGG GTATTCGGAC GAGAACATCA GTGATCTGGA CGACCTAAAG

CATCATCGGG AATCGATTAT TGAGCCCCAG TACGACACTT TCTGCCATGG CCATGCCACA

GCCATTTATA TAGACAAATT CTCGCGCTTT TTCTTCCCGT TTTCGTTCTT TATACTCAAT

ATTGTCTATT GGACAACGTT CCTATGATGG ATGGAAAAGT TTCTCCGAAG GAATAGAGCG

TAAACA.
```

The present invention also relates to the isolated or purified DNA molecule described in FIG. 5 (AC15-4) and set forth as SEQ ID NO:5, which encodes the *Drosophila* LGIC protein described in FIG. 7 and set forth as SEQ ID NO:7, the nucleotide sequence AC15-4 as follows:

```
AACTGCCAAG ACGTTTAGAA CGGAAAAACT GAATTTTCAA AAATATTTCG AGTAAACTGT    (SEQ ID NO:5)

TAAATGCTGA AGTGTTCTGA AATATTCCTT AAAACATAGA AACCTTCTTT GACATCTTTA

TAAAGCAATA AAATTCATTC GGGAAGTTTA TGAATAGTGG TGTTATTAAT CATGCCATTT

GTGGCGTCAA GCTGATGGTT ATGTAATCTC TGTGAAGATT CTAGAAATCC AACAGAAATA

TATTGCTTCG AAAACCAAGC AAAGATTACT TGACTGGAGA GGAAAGCTAT TTCGAATTCA

TCTAAAAACT GTAAAGAGTT CACATTAAAA TGGTGTTCCA AATAATAATC CTGGTGATCT

GCACCATCTG CATGAAGCAC TACGCCAAAG GGGAGTTTCA ACAAAGTCTG GCCATAACCG

ACATCCTGCC CGAGGACATC AAGCGTTACG ACAAGATGAG ACCGCCGAAG AAAGAGGGTC

AGCCGACGAT AGTCTACTTC CATGTGACTG TGATGGGTCT GGACTCCATT GATGAGAACT

CGATGACTTA TGTGGCGGAT GTGTTCTTTG CACAGACGTG GAAGGATCAT CGCCTGCGAT

TGCCGGAGAA TATGACACAG GAATACCGCC TGCTCGAGGT GGACTGGCTA AAAAATATGT

GGCGCCCGGA TTCGTTTTTC AAAAACGCCA AATCGGTGAC CTTTCAGACC ATGACAATAC

CCAATCACTA TATGTGGCTG TACAAGGATA AGACCATTCT CTATATGGTC AAGCTAACAC

TGAAGCTGTC CTGCATCATG AATTTCGCCA TTTATCCTCA TGACACACAG GAGTGCAAGC

TGCAAATGGA AAGCCTGTCC CACACCACGG ATGACTTGAT ATTCCAGTGG GATCCAACAA

CGCCCCTTGT GGTTGATGAA ACATCGAAC TGCCGCAGGT GGCCCTCATC CGGAATGAAA

CGGCGGACTG CACCCAGGTT TATTCCACTG GCAACTTCAC ATGCCTGGAG GTGGTGTTCA

CCCTTAAGCG TCGTTTGGTT TACTACGTTT TCAACACCTA CATTCCCACC TGCATGATAG
```

-continued

```
TGATCATGTC ATGGGTATCC TTCTGGATCA AACCGGAGGC GGCACCAGCC CGTGTGACTC

TGGGTGTCAC CTCCTTGCTA ACGCTTTCCA CGCAACACGC CAAATCGCAG TCGTCTTTGC

CACCTGTTTC CTATCTCAAG GCAGTGGACG CCTTTATGTC CGTTTGCACG GTGTTCGTGT

TTATGGCCCT CATGGAGTAT TGTCTAATAA ACATCGTCCT GAGCGACACG CCCATTCCCA

AGCCGATGGC TTATCCACCC AAACCTGTGG CGGGCGATGG GCCCAAGAAA GAGGGCGAGG

GTGCTCCTCC TGGGGCAGC AACTCGACGG CCAGCAAGCA ACAAGCCACC ATGTTGCCAC

TGGCCGATGA AAAGATCGAG AAAATTGAGA AGATCTTTGA CGAGATGACC AAGAATAGAA

GGATTGTAAC CACCACACGC CGCGTGGTGC GTCCACCATT GGACGCCGAT GGTCCGTGGA

TTCCGCGACA GGAGTCGCGG ATAATACTGA CCCCGACTAT CGCTCCGCCG CCACCGCCCC

CTCAGCCAGC GGCACCGGAA CCGGAACTAC CCAAGCCGAA ACTCACACCC GCCCAGGAGC

GGCTCAAGCG GGCTATATAT ATAGATCGGT CCTCGCGCGT CCTTTTCCCC GCCCTCTTCG

CCAGTCTGAA TGGCATCTAC TGGTGTGTGT TCTACGAGTA TCTATAAGGA CTACGACGAC

TGTGCCCTGT AAATACTTTC GCTAGCTCTC TGGCACTCCA TCCGAGTGTT AAACGTTGAT

TGTTCGCATA TATCGAAACG TGTATCGCAA ATTTAATCTT AAGCTTTCAC GCACAAGCTT

TAAGTCAATG AATTTTAAAC ATAGATTATT GTTAAACCAG AAGGAAGGAA TAATGGTACA

GATGGAGATC TGATTACAGG ATAAATTACA AATTATCAAT TCAATTCCTA AAATGCTTAA

AGTTAATCAA GTGACGTAGT AGCTGATGTA GCC.
```

The present invention also relates to the isolated or purified DNA molecule described in FIG. 6 (AC15-25), as set forth as SEQ ID NO:6, which also encodes the *Drosophila* LGIC protein described in FIG. 7 and set forth as SEQ ID NO:7, the nucleotide sequence AC15-25 as follows:

```
CGAGTAAACT GTTAAATGCT GAAGTGTTCT GAAATATTCC TTAAAACATA GAAACCTTCT   (SEQ ID NO:6)

TTGACATCTT TATAAAGCAA TAAAATTCAT TCGGGAAGTT TATGAATAGT GGTGTTATTA

ATCATGCCAT TTGTGGCGTC AAGCTGATGG TTATGTAATC TCTGTGAAGA TTCTAGAAAT

CCAACAGAAA TATATTGCTT CGAAAACCAA GCAAAGATTA CTTGACTGGA GAGGAAAGCT

ATTTCGAATT CATCTAAAAA CTGTAGCTCA CATTAAAATG GTGTTCCAAA TAATAATCCT

GGTGATCTGC ACCATCTGCA TGAAGCACTA CGCCAAAGGG GAGTTTCAAC AAAGTCTGGC

CATAACCGAC ATCCTGCCCG AGGACATCAA GCGTTACGAC AAGATGAGAC CGCCGAAGAA

AGAGGGTCAG CCGACGATAG TCTACTTCCA TGTGACTGTG ATGGGTCTGG ACTCCATTGA

TGAGAACTCG ATGACTTATG TGGCGGATGT GTTCTTTGCA CAGACGTGGA AGGATCATCG

CCTGCGATTG CCGGAGAATA TGACACAGGA ATACCGCCTG CTCGAGGTGG ACTGGCTAAA

AAATATGTGG CGGCCGGATT CGTTTTTCAA AAACGCCAAA TCGGTGACCT TTCAGACCAT

GACAATACCC AATCACTATA TGTGGCTGTA CAAGGATAAG CAACTTCTGT ACATGGTCAA

ACTAACACTG AAGCTGTCCT GCATCATGAA CTTCGCCATT TATCCTCATG ATACACAGGA

GTGCAAGCTG CAAATGGAAA GCCTGTCCCA CACCACGGAT GACTTGATAT TCAGTGGGA

TCCAACGACG CCCCTTGTGG TTGATGAAAA CATCGAGCTG CCGCAGGTGG CCCTCATCCG

AAATGAAACG GCGGACTGTA CCCAAGTTTA TTCCACTGGC AACTTCACAT GCCTGGAGGT

GGTGTTCACC CTTAAGCGTC GTTTGGTTTA CTACGTTTTC AACACCTACA TTCCCACCTG
```

-continued

```
CATGATAGTG ATCATGTCAT GGGTATCCTT CTGGATCAAA CCGGAGGCGG CACCAGCCCG

TGTGACTCTG GGTGTCACCT CCTTGCTAAC GCTTTCCACG CAACACGCCA AATCGCAGTC

GTCTTTGCCA CCTGTTTCCT ATCTCAAGGC AGTGGACGCC TTTATGTCCG TTTGCACGGT

GTTCGTGTTT ATGGCCCTCA TGGAGTATTG TCTAATAAAC ATCGTCCTGA GCGACACGCC

CATTCCCAAG CCGATGGCCT ATCCACCCAA ACCTGTGGCG GGAGATGGGC CCAAGAAAGA

GGGCGAGGGT GCTCCTCCTG GGGGCAGCAA CTCGACGGCC AGCAAGCAAC AAGCCACCAT

GTTGCCACTG GCCGATGAAA AGATCGAGAA AATTGAGAAG ATCTTTGACG AGATGACCAA

GAATAGAAGG ATTGTAACCA CCACACGCCG CGTGGTGCGT CCGCCATTGG ACGCCGATGG

TCCGTGGATT CCGCGACAGG AGTCGCGGAT AATACTGACC CCGACTATCG CTCCGCCGCC

ACCGCCCCCT CAGCCAGCGG CACCGGAACC GGAACTGCCC AAGCCGAAAC TCACACCCGC

CCAGGAGCGG CTCAAGCGGG CTATATATAT AGATCGGTCC TCGCGCGTCC TTTTCCCCGC

CCTCTTCGCC AGTCTGAATG GCATCTACTG GTGTGTGTTC TACGAGTATC TATAAGGACT

ACGACGACTG TGCCCTGTAA ATACTTTCGC TAGCTCTCTG GCACTCCATC CGAGTGTTAA

ACGTTGATTG TTCGCATATA TCGAAACGTG TATCGCAAAT TTAATCTTAA GCTTTCACGC

ACAAGCTTTA AGTCAATGAA TTTTAAACAT AGATTATTGT TAAACCAGAA GGAAGGAATA

ATGGTACAGA TGGAGATCTG ATTACAGGAT AAATTACAAA TTATCAATTC AATTCCTAAA

ATGCTTAAAG TTAATCAAGT GACGTAGTAG CTGATGTAGC CTAAGTGAAT TGTA.
```

The above-exemplified isolated DNA molecules, shown in FIG. 1, 3 and 5, respectively, comprise the following characteristics:

AC05-10 (SEQ ID NO:1):

1518 nuc. :initiating Met (nuc. 199–201) and "TGA" term. codon (nuc.1477–1479), the open reading frame resuting in an expressed protein of 426 amino acids, as set forth in SEQ ID NO:2.

AC05-11 (SEQ ID NO:3):

1506 nuc.:initiating Met (nuc. 199–201) and "TGA" term. codon (nuc. 1465–1467), the open reading frame resuting in an expressed protein of 422 amino acids, as set forth in SEQ ID NO:4.

AC15-4 (SEQ ID NO:5):

2133 nuc. :initiating Met (nuc. 330–332) and "TAA" term. codon (nuc. 1785–1787), the open reading frame resuting in an expressed protein of 485 amino acids, as set forth in SEQ ID NO:7.

AC15-25 (SEQ ID NO:6):

2034 nuc. :initiating Met (nuc. 278–280) and "TAA" term. codon (nuc. 1733–1735), the open reading frame resulting in an expressed protein of 485 amino acids, as set forth in SEQ ID NO:7.

The Ac5-10 and Ac5-11 open reading frames are identical, save for a 12 nucleotide insertion within Ac5-10 which encodes a 4 amino acid insertion within the M3-M4 intracellular loop in Ac05-10 (a Ser-Ala-Leu-Gln insertion from amino acid residue 375 through amino acid residue 378, as set forth in SEQ ID NO:2). Therefore, the AcS-10 protein is 426 amino acids in length while the Ac5-11 protein is 422 amino acids in length. Expression of Ac5-10 in Xenopus results in a functional ion channel that responds to the addition of histamine.

Two clones of Ac15 are disclosed. Ac15-4 (2073 bp) and Ac15-25 (2034 bp) predict the same protein sequence but differ in 16 silent nucleotide changes within the 1455 nucleotide open reading frame. The expressed protein from Ac15-4/Ac15-25 is 485 amino acids in length.

The present invention also relates to biologically active fragments or mutants of SEQ ID NOs:1, 3, 5 and 6 which encode mRNA expressing DmLGIC. Any such biologically active fragment and/or mutant will encode either a protein or protein fragment which at least substantially mimics the wild type protein, including but not limited to the wild type forms as set forth in SEQ ID NOs: 2, 4, and/or 7. Any such polynucleotide includes but is not necessarily limited to nucleotide substitutions, deletions, additions, amino-terminal truncations and carboxy-terminal truncations such that these mutations encode MRNA which express a protein or protein fragment of diagnostic, therapeutic or prophylactic use and would be useful for screening for agonists and/or antagonists for DmLGIC function.

A preferred aspect of this portion of the present invention is disclosed in FIGS. 1, 3, 5 and 6, which describes the four novel DNA molecules which encode three forms of DmLGIC proteins.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The degeneracy of the genetic code is such that, for all but two amino acids, more than a single codon encodes a particular amino acid. This allows for the construction of synthetic DNA that encodes the DmLGIC protein where the nucleotide sequence of the synthetic DNA differs significantly from the nucleotide sequence of SEQ ID NOs: 1, 3, 5 and 6 but still encodes the same DmLGIC protein as SEQ ID NO: 1, 3, 5 and 6. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the DmLGIC protein in the host. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Another source of sequence variation may occur through RNA editing, as discussed infra. Such RNA editing may result in another form of codon redundancy, wherein a change in the open reading frame does not result in an altered amino acid residue in the expressed protein. For whatever biological reason, a example can be found within the present disclosure. The cDNA clones Ac15-4 and Ac15-25 encode a 485 amino acid protein as set forth in SEQ ID NO: 7, but 16 silent nucleotide changes occur when comparing the Ac15-25 open reading frame sequence to the Ac15-4 open reading frame sequence. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

The present invention also relates to recombinant vectors and recombinant hosts, both prokaryotic and eukaryotic, which contain the substantially purified nucleic acid molecules disclosed throughout this specification. The nucleic acid molecules of the present invention encoding a DmLGIC protein, in whole or in part, can be linked with other DNA molecules, i.e, DNA molecules to which the DmLGIC coding sequence are not naturally linked, to form "recombinant DNA molecules" which encode a respective DmLGIC protein. The novel DNA sequences of the present invention can be inserted into vectors which comprise nucleic acids encoding DmLGIC or a functional equivalent. These vectors may be comprised of DNA or RNA; for most cloning purposes DNA vectors are preferred. Typical vectors include plasmids, modified viruses, bacteriophage, cosmids, yeast artificial chromosomes, and other forms of episomal or integrated DNA that can encode a DmLGIC protein. It is well within the purview of the skilled artisan to determine an appropriate vector for a particular gene transfer or other use.

Included in the present invention are DNA sequences that hybridize to SEQ ID NOs:1, 3, 5 and 6 under moderate to highly stringent conditions. By way of example, and not limitation, a procedure using conditions of high stringency is as follows: Prehybridization of filters containing DNA is carried out for 2 hours to overnight at 65° C. in buffer composed of 6×SSC, 5× Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5-20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes. Reagents mentioned in the foregoing procedures for carrying out high stringency hybridization are well known in the art. Details of the composition of these reagents can be found in, e.g., Sambrook et al., 1989, *Molecular Cloning: A Laboratory Manual*; Cold Spring Harbor Laboratory, Cold Spring Harbor, N.Y. In addition to the foregoing, other conditions of high stringency which may be used are well known in the art.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.,: (Computational Molecular Biology, Lesk, A. M., ed. Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds. Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptide sequences, the term "identity" is well known to skilled artisans (Carillo and Lipton, 1988, *SIAM J Applied Math* 48:1073). Methods commonly employed to determine identity or similarity between two sequences include, but are not limited to, those disclosed in Guide to Huge Computers, Martin J. Bishop, ed., Academic Press, San Diego, 1994, and Carillo and Lipton, 1988, *SIAM J Applied Math* 48:1073. Methods to determine identity and similarity are codified in computer programs. Preferred computer program methods to determine identity and similarity between two sequences include, but are not limited to, GCG program package (Devereux, et al, 1984, *Nucleic Acids Research* 12(1):387), BLASTN, and FASTA (Altschul, et al., 1990, *J Mol. Biol.* 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations or alternative nucleotides per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations or alternative nucleotide substitutions of the reference sequence may occur at the 5' or 3' terminal positions of the reference nucleotide sequence or anywhere between those terminal positions, interspersed either individually among nucleotides in the reference sequence or in one or more contiguous groups within the reference sequence. One source of such a "mutation" or change which results in a less than 100% identity may occur through RNA editing. The process of RNA editing results in modification of an MRNA molecule such that use of that modified mRNA as a template to generate a cloned cDNA may result in one or more nucleotide changes, which may or may not result in a codon change. This RNA editing is known to be catalyzed by an RNA editase. Such an RNA editase is RNA adenosine deaminase, which converts an adenosine residue to an inosine residue, which tends to mimic a cytosine residue. To this end, conversion of an mRNA residue from A to I will result in A to G transitions in the coding and noncoding regions of a cloned cDNA (e.g., see Hanrahan et al, 1999, *Annals New York Acad. Sci.* 868:51–66; for a review see Bass, 1997, TIBS 22: 157–162). Similarly, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence of anywhere between those terminal positions, interspersed either individually among residues in the reference sequence or in one or more contiguous groups within the reference sequence. Again, as noted above, RNA editing may result in a codon change which will result in an expressed protein which differs in "identity" from other proteins expressed from "non-RNA edited" transcripts, which correspond directly to the open reading frame of the genomic sequence.

The present invention also relates to a substantially purified form of a respective DmLGIC protein, which comprises the amino acid sequence disclosed in FIG. 2, FIG. 4 and FIG. 7, and as set forth in SEQ ID NOs:2, 4 and 7, respectively. The disclosed DmLGIC proteins contain an open reading frame of 426 amino acids (SEQ ID NO:2), 422 amino acids (SEQ ID NO:4) and 485 amino acids (SEQ ID NO:7) in length, as shown in FIGS. 2, 4 and 7, and as follows:

```
MQSPTSKLVE FRCLIALAIY LHALEQSIQH CHCVHGYRNN TESAELVSHY (SEQ ID NO:4)

ESSLSLPDIL PIPSKTYDKN RAPKLLGQPT VVYFHVTVLS LDSINEESMT

YVTDIFLAQS WRDPRLRLPE NMSEQYRILD VDWLHSIWRP DCFFKNAKKV

TFHEMSIPNH YLWLYHDKTL LYMSKLTLVL SCAMKFESYP HDTQICSMMI

ESLSHTVEDL VFIWNMTDPL VVNTEIELPQ LDISNNYTTD CTIEYSTGNF

TCLAIVFNLR RRLGYHLFHT YIPSALIVVM SWISFWIKPE AIPARVTLGV

TSLLTLATQN TQSQQSLPPV SPVKAIDVWM SSCSVFVFLS LMEFAVVNNF

MGPVATKAMK GYSDENISDL DDLKSALQHH RESIIEPQYD TFCHGHATAI

YIDKFSRFFF PFSFFILNIV YWTTFL*;
```

-continued

```
MQSPTSKLVE FRCLIALAIY LHALEQSIQH CHCVHGYRNN TESAELVSHY (SEQ ID NO:4)

ESSLSLPDIL PIPSKTYDKN RAPKLLGQPT VVYFHVTVLS LDSINEESMT

YVTDIFLAQS WRDPRLRLPE NMSEQYRILD VDWLHSIWRP DCFFKNAKKV

TFHEMSIPNH YLWLYHDKTL LYMSKLTLVL SCAMKFESYP HDTQICSMMI

ESLSHTVEDL VFIWNMTDPL VVNTEIELPQ LDISNNYTTD CTIEYSTGNF

TCLAIVFNLR RRLGYHLFHT YIPSALIVVM SWISFWIKPE AIPARVTLGV

TSLLTLATQN TQSQQSLPPV SYVKAIDVWM SSCSVFVFLS LMEFAVVNNF

MGPVATKAMK GYSDENISDL DDLKHHRESI IEPQYDTFCH GHATAIYIDK

FSRFFFPFSF FILNIVYWTT FL*;
and,

MVFQIIILVI CTICMKHYAK GEFQQSLAIT DILPEDIKRY DKMRPPKKEG (SEQ ID NO:7)

QPTIVYFHVT VMGLDSIDEN SMTYVADVFF AQTWKDHRLR LPENMTQEYR

LLEVDWLKNM WRPDSFFKNA KSVTFQTMTI PNHYMWLYKD KTILYMVKLT

LKLCCIMNFA IYPHDTQECK LQMESLSHTT DDLIFQWDPT TPLVVDENIE

LPQVALIRNE TADCTQVYST GNFTCLEVVF TLKRRLVYYV FNTYIPTCMI

VIMSWVSFWI KPEAAPARVT LGVTSLLTLS TQHAKSQSSL PPVSYLKAVD

AFMSVCTVFV FMALMEYCLI NIVLSDTPIP KPMAYPPKPV AGDGPKKEGE

GAPPGGSNST ASKQQATMLP LADEKIEKIE KIFDEMTKNR RIVTTTRRVV

RPPLDADGPW IPRQESRIIL TPTIAPPPPP PQPAAPEPEL PKPKLTPAQE

RLKRAIYIDR SSRVLFPALF ASLNGIYWCV FYEYL*.
```

The present invention also relates to biologically active fragments and/or mutants of the DmLGIC protein comprising the amino acid sequence as set forth in SEQ ID NOs:2, 4, and 7, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of DmLGIC function.

Another preferred aspect of the present invention relates to a substantially purified, fully processed LGIC protein obtained from a recombinant host cell containing a DNA expression vector comprises a nucleotide sequence as set forth in SEQ ID NOs: 1, 3, 5, and/or 6 and expresses the respective DmLGIC precursor protein. It is especially preferred that the recombinant host cell be a eukaryotic host cell, such as a mammalian cell line, or Xenopus oocytes, as noted above.

As with many proteins, it is possible to modify many of the amino acids of DmLGIC protein and still retain substantially the same biological activity as the wild type protein. Thus this invention includes modified DmLGIC polypeptides which have amino acid deletions, additions, or substitutions but that still retain substantially the same biological activity as a respective, corresponding DmLGIC. It is generally accepted that single amino acid substitutions do not usually alter the biological activity of a protein (see, e.g., Molecular Biology of the Gene, Watson et al., 1987, Fourth Ed., The Benjamin/Cummings Publishing Co., Inc., page 226; and Cunningham & Wells, 1989, Science 244: 1081-1085). Accordingly, the present invention includes polypeptides where one amino acid substitution has been made in SEQ ID NO:2, 4, and/or 7 wherein the polypeptides still retain substantially the same biological activity as a corresponding DmLGIC protein. The present invention also includes polypeptides where two or more amino acid substitutions have been made in SEQ ID NO:2, 4, or 7 wherein the polypeptides still retain substantially the same biological activity as a corresponding DmLGIC protein. In particular, the present invention includes embodiments where the above-described substitutions are conservative substitutions.

One skilled in the art would also recognize that polypeptides that are functional equivalents of DmLGIC and have changes from the DmLGIC amino acid sequence that are small deletions or insertions of amino acids could also be produced by following the same guidelines, (i.e, minimizing the differences in amino acid sequence between DmLGIC and related proteins. Small deletions or insertions are generally in the range of about 1 to 5 amino acids. The effect of such small deletions or insertions on the biological activity of the modified DmLGIC polypeptide can easily be assayed by producing the polypeptide synthetically or by making the required changes in DNA encoding DmLGIC and then expressing the DNA recombinantly and assaying the protein produced by such recombinant expression.

The present invention also includes truncated forms of DmLGIC which contain the region comprising the active site of the enzyme. Such truncated proteins are useful in various assays described herein, for crystallization studies, and for structure-activity-relationship studies.

The present invention also relates to membrane-containing crude lysates or substantially purified subcellular membrane fractions from the recombinant host cells (both prokaryotic and eukaryotic as well as both stably and transiently transformed cells) which contain the nucleic acid molecules of the present invention. These recombinant host cells express DmLGIC or a functional equivalent, which becomes post translationally associated with the cell membrane in a biologically active fashion. These subcellular membrane fractions will comprise either wild-type or mutant forms of DmLGIC at levels substantially above endogenous levels and hence will be useful in assays to select modulators of DmLGIC proteins or channels. In other words, a specific use for such subcellular membranes involves expression of DmLGIC within the recombinant cell followed by isolation and substantial purification of the membranes away from other cellular components and subsequent use in assays to select for modulators, such as agonist or antagonists of the protein or biologically active channel comprising one or more of the proteins disclosed herein. Alternatively, the lysed cells, containing the membranes, may be used directly in assays to select for modulators of the recombinantly expressed protein(s) disclosed herein. Therefore, another preferred aspect of the present invention relates to a substantially purified membrane preparation or lysed recombinant cell components which include membranes, which has been obtained from a recombinant host cell transformed or transfected with a DNA expression vector which comprises and appropriately expresses a complete open reading frame as set forth in SEQ ID NOs: 1, 3, 5, and/or 6, resulting in a functional, processed form of the respective single, homomultimer or heteromultimer DmLGIC receptor. It is especially preferred is that the recombinant host cell be a eukaryotic host cell, such as a mammalian cell line, or Xenopus oocytes, as noted above.

To this end, a preferred aspect of the present invention is a functional DmLGIC channel receptor, comprised of either a single channel protein or a channel comprising multiple subunits, referred to herein as a homomultimer channel or a heteromultimer channel. Therefore, a single channel may be comprised of a protein as disclosed in SEQ ID NOs: 2, 4 or 7, or a biologically active equivalent thereof (i.e., a altered channel protein which still functions in a similar fashion to that of a wild-type channel receptor). A homomultimer channel receptor complex will comprise more than one polypeptide selected from the disclosed group of SEQ ID NOs: 2, 4 and 7, as well as biologically active equivalents. A heteromultimer channel receptor complex will comprise multiple subunits wherein at least 2 of the 3 proteins disclosed herein contribute to channel formation, or where at least one of the proteins associates with additional proteins or channel components to provide for an active channel receptor complex. Therefore, the present invention additionally relates to substantially purified channels as described herein, as well as substantially purified membrane preparations, partially purified membrane preparations, or cell lysates which contain the functional single, homomultimer or heteromultimer channels described herein.

The present invention also relates to isolated nucleic acid molecules which are fusion constructions expressing fusion proteins useful in assays to identify compounds which modulate wild-type DmLGIC activity, as well as generating antibodies against DmLGIC. One aspect of this portion of the invention includes, but is not limited to, glutathione S-transferase (GST)-DmLGIC fusion constructs. Recombinant GST-DmLGIC fusion proteins may be expressed in various expression systems, including Spodoptera frugiperda (Sf21) insect cells (Invitrogen) using a baculovirus expression vector (pAcG2T, Pharmingen). Another aspect involves DmLGIC fusion constructs linked to various markers, including but not limited to GFP (Green fluorescent protein), the MYC epitope, and GST. Again, any such fusion constructs may be expressed in the cell line of interest and used to screen for modulators of one or more of the DmLGIC proteins disclosed herein.

A preferred aspect for screening for modulators of DmLGIC activity is an expression system for the electrophysiological-based assays for measuring ligand-gated ion channel activity comprising injecting the DNA molecules of the present invention into Xenopus laevis oocytes. The general use of Xenopus oocytes in the study of ion channel activity is known in the art (Dascal, 1987, Crit. Rev. Biochem. 22: 317—317; Lester, 1988, Science 241: 1057–1063; see also Methods of Enzymology, Vol. 207, 1992, Ch. 14–25, Rudy and Iverson, ed., Academic Press, Inc., New York). An improved method exists for measuring channel activity and modulation by agonists and/or antagonists which is several-fold more sensitive than previous techniques. The Xenopus oocytes are injected with nucleic acid material, including but not limited to DNA, mRNA or cRNA which encode a gated-channel, wherein channel activity may be measured as well as response of the channel to various modulators. Ion channel activity is measured by utilizing a holding potential more positive than the reversal potential for chloride (i.e, greater than −30 mV), preferably about 0 mV. This alteration in assay measurement conditions has resulting in a 10-fold increase in sensitivity of the assay to modulation by ivermectin phosphate. Therefore, this improved assay allows screening and selecting for compounds which modulate LGIC activity at levels which were previously thought to be undetectable.

Any of a variety of procedures may be used to clone DmLGIC. These methods include, but are not limited to, (1) a RACE PCR cloning technique (Frohman, et al., 1988, Proc. Natl. Acad. Sci. USA 85: 8998–9002). 5' and/or 3' RACE may be performed to generate a full-length cDNA sequence. This strategy involves using gene-specific oligonucleotide primers for PCR amplification of DmLGIC cDNA. These gene-specific primers are designed through identification of an expressed sequence tag (EST) nucleotide sequence which has been identified by searching any number of publicly available nucleic acid and protein databases; (2) direct functional expression of the DmLGIC cDNA following the construction of a DmLGIC-containing cDNA library in an appropriate expression vector system; (3) screening a DmLGIC-containing cDNA library constructed in a bacteriophage or plasmid shuttle vector with a labeled degenerate oligonucleotide probe designed from the amino acid sequence of the DmLGIC protein; (4) screening a DmLGIC-containing cDNA library constructed in a bacteriophage or plasmid shuttle vector with a partial cDNA encoding the DmLGIC protein. This partial cDNA is obtained by the specific PCR amplification of DmLGIC DNA fragments through the design of degenerate oligonucleotide primers from the amino acid sequence known for other kinases which are related to the DmLGIC protein; (5) screening a DmLGIC-containing cDNA library constructed in a bacteriophage or plasmid shuttle vector with a partial cDNA or oligonucleotide with homology to a mammalian DmLGIC protein. This strategy may also involve using gene-specific oligonucleotide primers for PCR amplification of DmLGIC cDNA identified as an EST as described above; or (6) designing 5' and 3' gene specific oligonucleotides using SEQ ID NO: 1, 3, and 5 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding DmLGIC. Alternatively, the DmLGIC cDNA may be cloned as described in Example Section 1. Briefly, partial sequences potentially encoding two novel ligand gated ion channel genes, AC05 and AC15, were identified in the *Drosophila* genome sequencing project using the Extended Smith Waterman algorithm. The query sequence was the *C. elegans* glutamate gated ion channel avr-15a peptide sequence (accession number-AJ000538), and the DNA database searched was publicly available *Drosophila* high throughput genomic sequences. The search was performed on a Compugen Biocel XLP hardware search engine (Petach Tikva, Israel). Both sequences entered into the database contained predicted introns. Primers specific to either Ac05 or Ac15 were designed based on the database sequences. With these primer combinations, RT-PCR on whole fly total RNA followed by TA cloning was performed for both genes. Fragments of approximately 500 bp in length for both Ac05 and Ac15 were isolated and verified by DNA sequencing. PolyA$^+$ RNA was purified from whole body Oregon R *Drosophila* and used to generate the double-stranded cDNA. 5' and 3' RACE fragments were obtained for both genes by 1$^{st}$ round PCR and nested PCR. The resulting fragment sizes were ~1.3 kb for Ac05 and ~1.8 kb for Ac15 in 3'-RACE. In 5'-RACE Ac05 and Ac15 both have fragment sizes of ~1 kb. The PCR products were cloned into a pCR2.1-TOPO vector. Miniprep DNA samples were screened by restriction digestion to separate spliced from unspliced clones. Using the sequences obtained from the 5' and 3' RACE products, PCR primers for both genes were designed to generate full-length clones. cDNA clones Ac05-10 and Ac05-11 were generated using primers Ac05 F1 and R1 for 1$^{st}$ round PCR and primers Ac05 F1 and R2 for 2$^{nd}$ round PCR. cDNA clones Ac15-4 and Ac15-25 were generated using primers Ac15 F1 and R1 for 1$^{st}$ round PCR. The PCR products were cloned into pCR2.1-TOPO vector. Two clones of Ac05 were identified: Ac05-10 (1518 bp) and Ac05-11(1506 bp). The clones are identical but for a 4 amino acid insertion within the M3-M4 intracellular loop in Ac05-10 (a Ser-Ala-Leu-Gln insertion from amino acid residue 375 through amino acid residue 378, as set forth in SEQ ID NO:2). Two clones of Ac15 were identified: Ac15-4 (2073 bp) and Ac15-25 (2034 bp), which predict the same protein sequence but differ in 16 nucleotides within 1455 nucleotide open reading frame.

It is readily apparent to those skilled in the art that other types of libraries, as well as libraries constructed from other cell types-or species types, may be useful for isolating a DmLGIC-encoding DNA or a DmLGIC homologue. Other types of libraries include, but are not limited to, cDNA libraries derived from other cells.

It is readily apparent to those skilled in the art that suitable cDNA libraries may be prepared from cells or cell lines which have DmLGIC activity. The selection of cells or cell lines for use in preparing a cDNA library to isolate a cDNA encoding DmLGIC may be done by first measuring cell-associated DmLGIC activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding DmLGIC may also be isolated from a suitable genomic DNA library. Construction of genomic DNA libraries can be performed by standard techniques well known in the art. Well known genomic DNA library construction techniques can be found in Sambrook, et al., supra. One may prepare genomic libraries, especially in P1 artificial chromosome vectors, from which genomic clones containing the DmLGIC can be isolated, using probes based upon the DmLGIC nucleotide sequences disclosed herein. Methods of preparing such libraries are known in the art (Ioannou et al., 1994, *Nature Genet.* 6:84–89).

In order to clone a DmLGIC gene by one of the preferred methods, the amino acid sequence or DNA sequence of a DmLGIC or a homologous protein may be necessary. To accomplish this, a respective DmLGIC protein may be purified and the partial amino acid sequence determined by automated sequenators. It is not necessary to determine the entire amino acid sequence, but the linear sequence of two regions of 6 to 8 amino acids can be determined for the PCR amplification of a partial DmLGIC DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the DmLGIC sequence but others in the set will be capable of hybridizing to DmLGIC DNA even in the presence of DNA oligonucleotides with mismatches. The mismatched DNA oligonucleotides may still sufficiently hybridize to the DmLGIC DNA to permit identification and isolation of DmLGIC encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1, 3, 5 or 6 either for the purpose of isolating overlapping 5' and 3' RACE products for generation of a full-length sequence coding for DmLGIC, or to isolate a portion of the nucleotide sequence coding for DmLGIC for use as a probe to screen one or more cDNA- or genomic-based libraries to isolate a full-length sequence encoding DmLGIC or DmLGIC-like proteins.

This invention also includes vectors containing a DmLGIC gene, host cells containing the vectors, and methods of making substantially pure DmLGIC protein comprising the steps of introducing the DmLGIC gene into a host cell, and cultivating the host cell under appropriate conditions such that DmLGIC is produced. The DmLGIC so produced may be harvested from the host cells in conventional ways. Therefore, the present invention also relates to methods of expressing the DmLGIC protein and biological equivalents disclosed herein, assays employing these gene products, recombinant host cells which comprise DNA constructs which express these proteins, and compounds identified through these assays which act as agonists or antagonists of DmLGIC activity.

The cloned DmLGIC cDNA obtained through the methods described above may be recombinantly expressed by molecular cloning into an expression vector (such as pcDNA3.neo, pcDNA3.1, pCR2.1, pCR2.1-TOPO, pBlue- BacHis2 or pLITMUS28, as well as other examples, listed infra) containing a suitable promoter and other appropriate transcription regulatory elements, and transferred into prokaryotic or eukaryotic host cells to produce recombinant DmLGIC. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. To determine the DmLGIC cDNA sequence(s) that yields optimal levels of DmLGIC, cDNA molecules including but not limited to the following can be constructed: a cDNA fragment containing the full-length open reading frame for DmLGIC as well as various constructs containing portions of the cDNA encoding only specific domains of the protein or rearranged domains of the protein. All constructs can be designed to contain none, all or portions of the 5' and/or 3' untranslated region of a DmLGIC cDNA. The expression levels and activity of DmLGIC can be determined following the introduction, both singly and in combination, of these constructs into appropriate host cells. Following determination of the DmLGIC cDNA cassette yielding optimal expression in transient assays, this DmLGIC cDNA construct is transferred to a variety of expression vectors (including recombinant viruses), including but not limited to those for mammalian cells, plant cells, insect cells, oocytes, bacteria, and yeast cells. Techniques for such manipulations can be found described in Sambrook, et al., supra, are well known and available to the artisan of ordinary skill in the art. Therefore, another aspect of the present invention includes host cells that have been engineered to contain and/or express DNA sequences encoding the DmLGIC. An expression vector containing DNA encoding a DmLGIC-like protein may be used for expression of DmLGIC in a recombinant host cell. Such recombinant host cells can be cultured under suitable conditions to produce DmLGIC or a biologically equivalent form. Expression vectors may include, but are not limited to, cloning vectors, modified cloning vectors, specifically designed plasmids or viruses. Commercially available mammalian expression vectors which may be suitable for recombinant DmLGIC expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAI-amp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUC-Tag (ATCC 37460), and lZD35 (ATCC 37565). Also, a variety of bacterial expression vectors may be used to express recombinant DmLGIC in bacterial cells. Commercially available bacterial expression vectors which may be suitable for recombinant DmLGIC expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant DmLGIC in fungal cells. Commercially available fungal cell expression vectors which may be suitable for recombinant DmLGIC expression include but are not limited to pYES2 (Invitrogen) and *Pichia* expression vector (Invitrogen). Also, a variety of insect cell expression vectors may be used to express recombinant protein in insect cells. Commercially available insect cell expression vectors which may be suitable for recombinant expression of DmLGIC include but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli,* fungal cells such as yeast, mammalian cells including, but not limited to, cell lines of bovine, porcine, monkey and rodent origin; and insect cells including but not limited to *Drosophila* and silkworm derived cell lines. For instance, one insect expression system utilizes *Spodoptera frugiperda* (Sf21) insect cells (Invitrogen) in tandem with a baculovirus expression vector (pAcG2T, Pharmingen). Also, mammalian species which may be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

The specificity of binding of compounds showing affinity for DmLGIC is shown by measuring the affinity of the compounds for recombinant cells expressing the cloned receptor or for membranes from these cells. Expression of the cloned receptor and screening for compounds that bind to DmLGIC or that inhibit the binding of a known, radiolabeled ligand of DmLGIC to these cells, or membranes prepared from these cells, provides an effective method for the rapid selection of compounds with high affinity for DmLGIC. Such ligands need not necessarily be radiolabeled but can also be nonisotopic compounds that can be used to displace bound radiolabeled compounds or that can be used as activators in functional assays. Compounds identified by the above method are likely to be agonists or antagonists of DmLGIC and may be peptides, proteins, or non-proteinaceous organic molecules.

Accordingly, the present invention is directed to methods for screening for compounds which modulate the expression of DNA or RNA encoding a DmLGIC protein as well as compounds which effect the function of the DmLGIC protein. Methods for identifying agonists and antagonists of other receptors are well known in the art and can be adapted to identify agonists and antagonists of a DmLGIC channel. For example, Cascieri et al. (1992, *Molec. Pharmacol.* 41:1096–1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to DmLGIC is measured, such binding can be measured by employing a labeled substance or agonist. The substance or agonist can be labeled in any convenient manner known to the art, e.g., radioactively, fluorescently, enzymatically.

As noted above in regard to the use of *Xenopus* oocytes to express a DmLGIC gene of interest, the present invention is directed to methods for screening for compounds which modulate the expression of DNA or RNA encoding a DmLGIC protein. Compounds which modulate these activities may be DNA, RNA, peptides, proteins, or non-proteinaceous organic molecules. Compounds may modulate by increasing or attenuating the expression of DNA or RNA encoding DmLGIC, or the function of the DmLGIC-based channels. Compounds that modulate the expression of DNA or RNA encoding DmLGIC or the biological function (i.e., channel activation by histamine or other ligands and/or compounds which activate the wild type channel) thereof may be detected by a variety of assays. The assay may be a simple "yes/no" assay to determine whether there is a change in expression or function. The assay may be made quantitative by comparing the expression or function (i.e., effect of channel activity) of a test sample with the levels of expression or function in a standard sample. Kits containing DmLGIC, antibodies to DmLGIC, or modified DmLGIC may be prepared by known methods for such uses.

To this end, the present invention relates in part to methods of identifying a substance which modulates DmLGIC receptor activity, which involves:

(a) combining a test substance in the presence and absence of a DmLGIC receptor protein wherein said DmLGIC receptor protein comprises the amino acid sequence as set forth in SEQ ID NO:, 4, and/or 7; and, (b) measuring and comparing the effect of the test substance in the presence and absence of the DmLGIC receptor protein.

In addition, several specific embodiments are disclosed herein to show the diverse type of screening or selection assay which the skilled artisan may utilize in tandem with an expression vector directing the expression of the DmLGIC receptor protein. Methods for identifying agonists and antagonists of other receptors are well known in the art and can be adapted to identify agonists and antagonists of DmLGIC. Therefore, these embodiments are presented as examples and not as limitations. To this end, the present invention includes assays by which DmLGIC modulators (such as agonists and antagonists) may be identified. Accordingly, the present invention includes a method for determining whether a substance is a potential agonist or antagonist of DmLGIC that comprises:

(a) transfecting or transforming cells with an expression vector that directs expression of DmLGIC in the cells, resulting in test cells;

(b) allowing the test cells to grow for a time sufficient to allow DmLGIC to be expressed and for a functional channel to be generated;

(c) exposing the cells to a labeled ligand of DmLGIC in the presence and in the absence of the substance;

(d) measuring the binding of the labeled ligand to the DmLGIC channel; where if the amount of binding of the labeled ligand is less in the presence of the substance than in the absence of the substance, then the substance is a potential agonist or antagonist of DmLGIC.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells may be harvested and resuspended in the presence of the substance and the labeled ligand. In a modification of the above-described method, step (c) is modified in that the cells are not harvested and resuspended but rather the radioactively labeled known agonist and the substance are contacted with the cells while the cells are attached to a substratum, e.g., tissue culture plates.

The present invention also includes a method for determining whether a substance is capable of binding to DmLGIC, i.e., whether the substance is a potential agonist or an antagonist of DmLGIC channel activation, where the method comprises:

(a) transfecting or transforming cells with an expression vector that directs the expression of DmLGIC in the cells, resulting in test cells;

(b) exposing the test cells to the substance;

(c) measuring the amount of binding of the substance to DmLGIC;

(d) comparing the amount of binding of the substance to DmLGIC in the test cells with the amount of binding of the substance to control cells that have not been transfected with DmLGIC;

wherein if the amount of binding of the substance is greater in the test cells as compared to the control cells, the substance is capable of binding to DmLGIC. Determining whether the substance is actually an agonist or antagonist can then be accomplished by the use of functional assays such as, e.g., the assay involving the use of promiscuous G-proteins described below.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells are harvested and resuspended in the presence of the substance.

The above described assays may be functional assays, where electrophysiological assays (e.g., see Example 2) may be carried out in transfected mammalian cell lines as well as *Xenopus* oocytes to measure the various effects test compounds may have on the ability of a known ligand (such as histamine or glutamate) to activate the channel, or for a test compound to modulate activity in and of itself (similar to the effect of ivermectin on known GluCl channels). Therefore, the skilled artisan will be comfortable adapting the cDNA clones of the present invention to known methodology to both initially and secondary screens to select for compounds that bind and/or activate the functional DmLGIC channels of the present invention.

The DNA molecules, RNA molecules, recombinant protein and antibodies of the present invention may be used to screen and measure levels of DmLGIC. The recombinant proteins, DNA molecules, RNA molecules and antibodies lend themselves to the formulation of kits suitable for the detection and typing of DmLGIC. Such a kit would comprise a compartmentalized carrier suitable to hold in close confinement at least one container. The carrier would further comprise reagents such as recombinant DmLGIC or anti-DmLGIC antibodies suitable for detecting DmLGIC. The carrier may also contain a means for detection such as labeled antigen or enzyme substrates or the like.

The assays described above can be carried out with cells that have been transiently or stably transfected with DmLGIC. The expression vector may be introduced into host cells via any one of a number of techniques including but not limited to transformation, transfection, protoplast fusion, and electroporation. Transfection is meant to include any method known in the art for introducing DmLGIC into the test cells. For example, transfection includes calcium phosphate or calcium chloride mediated transfection, lipofection, infection with a retroviral construct containing DmLGIC, and electroporation. The expression vector-containing cells are individually analyzed to determine whether they produce DmLGIC protein. Identification of DmLGIC expressing cells may be done by several means, including but not limited to immunological reactivity with anti-Dm-LGIC antibodies, labeled ligand binding, and/or the presence of host cell-associated DmLGIC activity.

The specificity of binding of compounds showing affinity for DmLGIC is shown by measuring the affinity of the compounds for recombinant cells expressing the cloned receptor or for membranes from these cells. Expression of the cloned receptor and screening for compounds that bind to DmLGIC or that inhibit the binding of a known, radiolabeled ligand of DmLGIC to these cells, or membranes prepared from these cells, provides an effective method for the rapid selection of compounds with high affinity for DmLGIC. Such ligands need not necessarily be radiolabeled but can also be nonisotopic compounds that can be used to displace bound radiolabeled compounds or that can be used as activators in functional assays. Compounds identified by the above method are likely to be agonists or antagonists of DmLGIC and may be peptides, proteins, or non-proteinaceous organic molecules.

Accordingly, the present invention is directed to methods for screening for compounds which modulate the expression of DNA or RNA encoding a DmLGIC protein as well as compounds which effect the function of the DmLGIC protein. Methods for identifying agonists and antagonists of other receptors are well known in the art and can be adapted to identify agonists and antagonists of DmLGIC. For example, Cascieri et al. (1992, *Molec. Pharmacol.* 41:1096–1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to is measured, such binding can be measured by employing a labeled substance or agonist. The substance or agonist can be labeled in any convenient manner known to the art, e.g., radioactively, fluorescently, enzymatically.

Therefore, the specificity of binding of compounds having affinity for DmLGIC shown by measuring the affinity of the compounds for recombinant cells expressing the cloned receptor or for membranes from these cells. Expression of the cloned receptor and screening for compounds that bind to DmLGIC or that inhibit the binding of a known, radiolabeled ligand of DmLGIC (such as glutamate, ivermectin or nodulasporic acid) to these cells, or membranes prepared from these cells, provides an effective method for the rapid selection of compounds with high affinity for DmLGIC. Such ligands need not necessarily be radiolabeled but can also be nonisotopic compounds that can be used to displace bound radiolabeled compounds or that can be used as activators in functional assays. Compounds identified by the above method again are likely to be agonists or antagonists of DmLGIC and may be peptides, proteins, or non-proteinaceous organic molecules. As noted elsewhere in this specification, compounds may modulate by increasing or attenuating the expression of DNA or RNA encoding DmLGIC, or by acting as an agonist or antagonist of the DmLGIC receptor protein. Again, these compounds that modulate the expression of DNA or RNA encoding DmLGIC or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample.

Expression of DmLGIC DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of DmLGIC in a host cell, DmLGIC protein may be recovered to provide DmLGIC protein in active form. Several DmLGIC protein purification procedures are available and suitable for use. Recombinant DmLGIC protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant DmLGIC protein can be separated from other cellular proteins by use of an immunoaffinity column made with monoclonal or polyclonal antibodies specific for full-length DmLGIC protein, or polypeptide fragments of DmLGIC protein.

Polyclonal or monoclonal antibodies may be raised against DmLGIC or a synthetic peptide (usually from about 9 to about 25 amino acids in length) from a portion of DmLGIC as disclosed in SEQ ID NOs:2, 4, and/or 7. Monospecific antibodies to DmLGIC are purified from mammalian antisera containing antibodies reactive against DmLGIC or are prepared as monoclonal antibodies reactive with DmLGIC using the technique of Kohler and Milstein (1975, *Nature* 256: 495–497). Monospecific antibody as used herein is defined as a single antibody species or multiple antibody species with homogenous binding characteristics for DmLGIC. Homogenous binding as used herein refers to the ability of the antibody species to bind to a specific antigen or epitope, such as those associated with DmLGIC, as described above. Human DmLGIC-specific antibodies are raised by immunizing animals such as mice, rats, guinea pigs, rabbits, goats, horses and the like, with an appropriate concentration of DmLGIC protein or a synthetic peptide generated from a portion of DmLGIC with or without an immune adjuvant.

Preimmune serum is collected prior to the first immunization. Each animal receives between about 0.1 mg and about 1000 mg of DmLGIC protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of DmLGIC protein or peptide fragment thereof in, preferably, Freund's complete adjuvant at multiple sites either subcutaneously (SC), intraperitoneally (IP) or both. Each animal is bled at regular intervals, preferably weekly,. to determine antibody titer. The animals may or may not receive booster injections following the initial immunization. Those animals receiving booster injections are generally given an equal amount of DmLGIC in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with DmLGIC are prepared by immunizing inbred mice, preferably Balb/c, with DmLGIC protein. The mice are immunized by the IP or SC route with about 1 mg to about 100 mg, preferably about 10 mg, of DmLGIC protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of DmLGIC in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using DmLGIC as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications,* Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-DmLGIC mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of DmLGIC in body fluids or tissue and cell extracts.

It is readily apparent to those skilled in the art that the above described methods for producing monospecific antibodies may be utilized to produce antibodies specific for DmLGIC peptide fragments, or a respective full-length DmLGIC.

DmLGIC antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length DmLGIC or DmLGIC protein fragments are slowly passed through the column. The column is then washed with phosphate buffered saline until the optical density ($A_{280}$) falls to background, then the protein is eluted with 0.23 M glycine-HCl (pH 2.6). The purified DmLGIC protein is then dialyzed against phosphate buffered saline.

The present invention also relates to a non-human transgenic animal which is useful for studying the ability of a variety of compounds to act as modulators of DmLGIC, or any alternative functional DmLGIC in vivo by providing cells for culture, in vitro. In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art. A type of target cell for transgene introduction is the embryonic stem cell (ES). ES cells can be obtained from pre-implantation embryos cultured in vitro and fused with embryos (Evans et al., 1981, *Nature* 292: 154–156; Bradley et al., 1984, *Nature* 309:255–258; Gossler et al., 1986, *Proc. Natl. Acad. Sci. USA* 83:9065–9069; and Robertson et al., 1986 *Nature* 322:445–448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468–1474). It will also be within the purview of the skilled artisan to produce transgenic or knock-out invertebrate animals (e.g., *C. elegans*) which express the DmLGIC transgene in a wild type *C. elegans* LGIC background as well in *C. elegans* mutants knocked out for one or both of the *C. elegans* LGIC subunits.

Pharmaceutically useful compositions comprising modulators of DmLGIC may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified DmLGIC, or either DmLGIC agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to illustrate the present invention without, however, limiting the same hereto.

EXAMPLE 1

Isolation and Characterization of DNA Molecules Encoding DmLGIC

The molecular procedures were performed following standard procedures well known in the art available in references such as Ausubel et. al. (1992, Short protocols in molecular biology. F. M. Ausubel et al.,—$2^{nd}$. ed. (John Wiley & Sons)) and Sambrook et al.(1989, Molecular cloning. A laboratory manual. J. Sambrook, E. F. Fritsch, and T. Maniatis—$2^{nd}$ ed. (Cold Spring Harbor Laboratory Press)).

Ac05 and Ac15 Database Search—Partial sequences potentially encoding two novel ligand gated ion channel genes, AC05 and AC15, were identified in the *Drosophila* genome sequencing project using the Extended Smith Waterman algorithm. The query sequence was the *C. elegans* glutamate gated ion channel avr-15a peptide sequence (accession number-AJ000538), and the DNA database searched was publicly available *Drosophila* high throughput genomic sequences. The search was performed on a Compugen Biocel XLP hardware search engine (Petach Tikva, Israel).

Both sequences entered into the database contained predicted introns. Primers specific to either 05 or 15 were designed based on the database sequences and synthesized. They are as follows:

```
1. ac05F1:
5'-CTT GCA CAA AGC TGG CGT G-3',      [SEQ ID NO:8]
(ac007805)

2. ac05F2:
5'-GTG AGC AGT ATC GCA TAT TG-3',     [SEQ ID N0:9]
(ac007805;

3. ac05R1:
5'-GTA GTT ATT TGA TAT GTC TAG C-3',  [SEQ ID NO:10]
(ac007805);

4. ac05R2:
5'-ACC TGT TGA GTA CTC TAT AG-3',     [SEQ IDNO:11]
(ac007805);

5. ac15F1:
5'-TTT GCA CAG ACG TGG AAG G-3',      [SEQ ID NO:12]
(ac007815);
```

-continued 6. ac15F2:
5'-ACA GGA ATA CCG CCT GCT C-3', [SEQ ID NO:13]
(ac007815);
and, 7. ac15R1:
5'-TTC ATT TCG GAT GAG GGC CAC-3' [SEQ ID NO:14]
(ac007815);

With these primer combinations, RT-PCR on whole fly total RNA followed by TA cloning was performed for both genes. Fragment of approximately 500 bp for both Ac05 and Ac15 were isolated and verified by sequencing.

5' and 3' RACE for Ac05 and Ac15—The Marathon® cDNA Amplification Kit from Clontech (Palo Alto, Calif.) was used as the primary tool for both 5'- and 3'-RACE reactions. PolyA$^+$ RNA was purified from whole body Oregon R *Drosophila* by Oligotex® mRNA Midi Kit (Qiagen, Santa Clarita, Calif.) and used to generate the double-stranded cDNA following the manufacturer's protocol. The following primers were used for RACE reactions:

3'-RACE Forward Primers:

Ac05:

1. Ac05GSPF1-5'-CAT CTT CCT TGC ACA AAG CTG GCG TG-3' [SEQ ID NO:15], (ac007805);
2. Ac05NGSPF2-5'-CAT GAG TGA GCA GTA TCG CAT ATT G-3' [SEQ ID NO:16], (ac007805);

Ac15:

1. Ac15GSPF1-5'-TGT GTT CTT TGC ACA GAC GTG GAA GG-3' [SEQ ID NO: 17] (ac007815).
2. Ac15NGSPF2 5'-TAT GAC ACA GGA ATA CCG CCT GCT C-3' [SEQ ID NO: 18] (ac007815).

5'-RACE Reverse Primers:

Ac05:

1. Ac05GSPR1: 5'-GTC TAG CTG CGG CAA CTC AAT CTC CGT G-3' [SEQ ID NO: 19], (ac007805);
2. Ac05NGSPR2: 5'-CTC GAT CAT CAT GGA GCA GAT TTG CGT G-3' [SEQ ID NO:20], (ac007805).

Ac15:

1. Ac15GSPR1: 5'-CGC CGT TTC ATT TCG GAT GAG GGC CAC-3' [SEQ ID NO:21], (ac007815 84958 bp–84984 bp);
2. Ac15NGSPR2: 5'-CAG GCT TTC CAT TTG CAG CTT GCA CTC C-3' [SEQ ID NO:22], (ac007815). This primer spans a splice junction, and the existence of this continuous sequence was available only from the sequence data of the Ac15 fragment described above.

5' and 3' RACE fragments were obtained for both genes by 1st round PCR and nested PCR based on the protocol of the Marathon® Kit, with a modification of the 5'RACE PCR cycle: 1 cycle of 1 minute at 94° C.; 5 cycles of 1 minute at 94° C. and 4 minutes at 72° C.; and 25 cycles of 1 minute at 94° C., 1 minutes at 68° C., and 3 minute at 72° C. The resulting fragment sizes were ~1.3 kb for Ac05 and ~1.8 kb for Ac15 in 3'-RACE. In 5'- RACE Ac05 and Ac15 both have fragment sizes of ~1 kb. The PCR products were cloned into pCR2.1-TOPO vector using the TOPO® TA Cloning Kit (Invitrogen, Carlsbad, Calif.). Miniprep DNA samples were screened by restriction digestion to separate spliced from unspliced clones. For the 3' ends, 6 and 8 samples of Ac05 and Ac15, respectively, were sequenced. For the 5' ends, 5 and 8 samples of Ac05 and Ac15 were sequenced.

Generation of Full-Length Clones—Using the sequences obtained from the 5' and 3' RACE products, PCR primers for both genes were designed to generate full-length clones. Forward primers and reverse primers for both AcO5 and Ac15 were designed as follows:

Ac05FullF1:
[SEQ ID NO:23]
5'-CAA TCG TCG CGA TAA CTC TGC CG-3';

Ac05FullR1:
[SEQ ID NO:24]
5'-CCT TTA TTT ATA CAC TAC ATG GTA ATC-3';

Ac05FullR2:
[SEQ ID NO:25]
5'-TGT TTA CGC TCT ATT CCT TCG GAG-3';

Ac15FullF1:
[SEQ ID NO:26]
5'-AAC TGC CAA GAC GTT TAG AAC GG-3';

Ac15FullF2:
[SEQ ID NO:27]
5'-CGA GTA AAC TGT TAA ATG CTG AAG TG-3';

Ac15FullR1:
[SEQ ID NO:28]
5'-TAC AAT TCA CTT AGG CTA CAT CAG C-3';
and,

Ac15FullR2:
[SEQ ID NO:29]
5'-GGC TAC ATC AGC TAC TAC GTC AC-3'.

The Advantage® 2 PCR Kit (Clonetech, Palo Alto, Calif.) was used for 1$^{st}$ and 2$^{nd}$ round PCR. cDNA clones Ac05-10 and Ac05-11 were generated using primers Ac05 F1 and R1 for 1$^{st}$ round PCR and primers Ac05 F1 and R2 for 2$^{nd}$ round PCR. cDNA clones Ac15-4 and Ac15-25 were generated using primers Ac15 F1 and R1 for 1$^{st}$ round PCR. 1$^{st}$ round PCR conditions were as follows: 1 cycle of 2 min at 94° C.; 5 cycles of 30 sec at 94° C., and 2 min 30sec at 72° C.; 25 cycles at 30 sec at 94° C., 1 min at 68° C., and 1 min 30 sec at 72° C.; and 1 cycle at 5 min at 72° C. For 2$_{nd}$ round PCR, primers Ac15 F1 and R2 were used for clone Ac15-4, and primers Ac15 F2 and R1 were used for clone Ac15-25. 2 µl of the first PCR product were used as template in a total reaction volume of 50 µl. 2$^{nd}$ round PCR conditions were as follows: 1 cycle of 2 min at 94° C.; 5 cycles of 30 sec at 94° C., 1 min at 68° C., and 1 min 30 sec at 72° C.; 5 cycles of 30 sec at 94° C., 1 min at 65° C., and 1 min 30sec at 72° C.; 20 cycles of 30 sec at 94° C., 1 min at 60° C., and 1 min 30 sec at 72° C.; and 1 cycle of 5 min at 72° C. One major band of ~1.5 kb was isolated for Ac05 and ~2 kb for Ac15. The PCR products were cloned into pCR2.1-TOPO vector using the TOPO® TA Cloning Kit (Invitrogene, Carlsbad, Calif.).

Two clones of Ac05 were identified: Ac05-10 (1518 bp) and Ac05-11 (1506 bp). The clones are identical but for a 4 amino acid insertion within the M3-M4 intracellular loop in Ac05-10. Two clones of Ac15 have been identified: Ac15-4 (2073 bp) and Ac5-25 (2034 bp), which predict the same protein sequence but differ in 16 nucleotides.

Synthesis of in vitro transcribed capped RNA—A PCR strategy was used to add both the T7 promoter upstream of the initiating methionine (ATG), and a polyA$^+$ tail following the stop codon (TGA and TAA for Ac05 and Ac15) of the open reading frame (ORF) of clones Ac05-10, Ac05-11 and Ac15-4, Ac15-25. The primers employed are:

Ac05:
Ac05T7:
5'-TAA TAC GAC TCA CTA TAG GGA GGG TGT TCA TAA TGC AAA GCC-3'; [SEQ ID NO:30]
and, Ac05dT,
5'-TTT TTT TTT TTT TTT TTT TTC ATA GGA ACG TTG TCC AAT AGA C-3'. [SEQ ID NO:31]

Ac15:
AC15T7:
5'-TAA TAC GAC TCA CTA TAG GGA GGC ACA TTA AAA TGG TGT TC-3'; [SEQ ID NO:32]
and, AC15dT:
5'-TTT TTT TTT TTT TTT TTT TTC CTT ATA GAT ACT CGT AGA AC-3'. [SEQ ID NO:33]

Amplified ORFs which contained both the T7 promoter and polyA+ tail were purified using the Qiaquick PCR Purification Kit (Qiagen, Germany), and used directly as templates in the in vitro transcription reaction (mMessage mMachine™, Ambion, Austin, Tex.) following the manufacturer's protocol. After removal of the DNA template, the RNA was extracted with phenol/CHCl$_3$, precipitated with LiCl, and resuspended in nuclease-free water at a storage concentration of 0.5 µg/µl.

EXAMPLE 2

Functional Expression of DmLGICs Clones in *Xenopus* Oocytes

Full length cDNA clones corresponding to the selected RT-PCR sequences were used as template for synthesis of in vitro transcribed RNA (Ambion Inc.). The capped cRNA transcripts are synthesized using appropriate oligonucleotide primers and the mMESSAGE mMACHINE in vitro RNA transcription kit from Ambion. *Xenopus laevis* oocytes were prepared and injected using standard methods as described (Arena et al., 1991, *Mol. Pharmacol.* 40: 368–374; Arena et al, 1992, *Mol. Brain Res.* 15: 339–348). Adult female *Xenopus laevis* were anesthetized with 0.17% tricaine methanesulfonate and the ovaries were surgically removed and placed in a dish consisting of (mM): NaCl 82.5, KCl 2, MgCl$_2$ 1, CaCl$_2$ 1.8, HEPES 5, adjusted to pH 7.5 with NaOH (OR-2). Ovarian lobes were broken open, rinsed several times, and gently shaken in OR-2 containing 0.2% collagenase (Sigma, Type 1A) for 2–5 hours. When approximately 50% of the follicular layers were removed, Stage V and VI oocytes were selected and placed in media consisting of (mM): NaCl 86, KCl 2, MgCl$_2$ 1, CaCl$_2$ 1.8, HEPES 5, Na pyruvate 2.5, theophylline 0.5, gentamicin 0.1 adjusted to pH 7.5 with NaOH (ND-96) for 24–48 hours before injection. For most experiments, oocytes were injected with 10 ng of cRNA in 50 nl of RNase free water. Control oocytes were injected with 50 nl of water. Oocytes were incubated for 1–5 days in ND-96 supplemented with 50 mg/ml gentamycin, 2.5 mM Na pyruvate and 0.5 mM theophylline before recording. Incubations and collagenase digestion were carried out at 18° C.

Voltage-clamp studies were conducted with the two microelectrode voltage clamp technique using a Dagan CA1 amplifier (Dagan Instruments, Minneapolis, Minn.). The current passing microelectrodes were filled with 0.7 M KCl plus 1.7 M K$_3$-citrate and the voltage recording microelectrodes were filled with 1.0 M KCl. The extracellular solution for most experiments was saline consisting of (mM): NaCl 96, BaCl$_2$ 3.5, MgCl$_2$ 0.5, CaCl$_2$ 0.1, HEPES 5, adjusted to pH 7.5 with NaOH. The extracellular chloride concentration was reduced in some experiments by equimolar replacement of NaCl with the sodium salt of the indicated anion. Experiments were conducted at 21–24° C. Data were acquired using the program Pulse and most analysis was performed with the companion program Pulsefit (Instrutech Instruments, Great Neck, N.Y.) or with Igor Pro (Wavemetrics, Lake Oswego, Ore.). Data were filtered ($f_c$, −3 db) at 1 kHz, unless otherwise indicated. FIG. 8 shows the results of the experiment in which the clone DmLGIC AC05 clone was expressed in a *Xenopus* oocyte. The measurement was made as described in this Example with the two microelectrode voltage clamp technique and the membrane potential was held at 0 mV. The bar at top shows the duration of application of histamine. This indicates that expression of this protein reconstitutes a functional ion channel that responds to the addition of histamine.

Expression of the AC15 clone in a *Xenopus* oocyte also forms a functional single channel protein which, as with AC05, responds to the addition of histamine.

EXAMPLE 3

Functional Expression of DmLGICs Clones in Mammalian Cells

A DmLGIC may be subcloned into a mammalian expression vector and used to transfect the mammalian cell line of choice. Stable cell clones are selected by growth in the presence of G418. Single G418 resistant clones are isolated and tested to confirm the presence of an intact DmLGIC gene. Clones containing the DmLGICs are then analyzed for expression using immunological techniques, such as immuneprecipitation, Western blot, and immunofluorescence using antibodies specific to the DmLGIC proteins. Antibody is obtained from rabbits innoculated with peptides that are synthesized from the amino acid sequence predicted from the DmLGIC sequences. Expression is also analyzed using patch clamp electrophysiological techniques and an anion flux assay.

Cells that are expressing DmLGIC stably or transiently, are used to test for expression of active channel proteins. These cells are used to identify and examine other compounds for their ability to modulate, inhibit or activate the respective channel.

Cassettes containing the DmLGIC cDNA in the positive orientation with respect to the promoter are ligated into appropriate restriction sites 3' of the promoter and identified by restriction site mapping and/or sequencing. These cDNA expression vectors may be introduced into fibroblastic host cells, for example, COS-7 (ATCC# CRL1651), and CV-1 tat [Sackevitz et al.,1987, *Science* 238: 1575], 293, L (ATCC# CRL6362) by standard methods including but not limited to electroporation, or chemical procedures (cationic liposomes, DEAE dextran, calcium phosphate). Transfected cells and cell culture supernatants can be harvested and analyzed for DmLGIC expression as described herein.

All of the vectors used for mammalian transient expression can be used to establish stable cell lines expressing DmLGIC. Unaltered DmLGIC cDNA constructs cloned into expression vectors are expected to program host cells to make DmLGIC protein. In addition, DmLGIC is expressed extracellularly as a secreted protein by ligating DmLGIC cDNA constructs to DNA encoding the signal sequence of a secreted protein. The transfection host cells include, but are not limited to, CV-1-P [Sackevitz et al.,1987, *Science* 238: 1575], tk-L [Wigler, et al., 1977, *Cell* 11: 223 ], NS/0, and dHFr-CHO [Kaufman and Sharp, 1982, *J. Mol. Biol.* 159: 601].

Co-transfection of any vector containing a DmLGIC cDNA with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of DmLGIC are quantitated by the assays described herein. DmLGIC cDNA constructs may also be ligated into vectors containing amplifiable drug-resistance markers for the production of mammalian cell clones synthesizing the highest possible levels of DmLGIC. Following introduction of these constructs into cells, clones containing the plasmid are selected with the appropriate agent, and isolation of an over-expressing clone with a high copy number of plasmids is accomplished by selection with increasing doses of the agent. The expression of recombinant DmLGIC is achieved by transfection of full-length DmLGIC cDNA into a mammalian host cell.

EXAMPLE 4

Cloning of DmLGIC cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). A recombinant baculoviruse expressing DmLGIC cDNA is produced by the following standard methods (InVitrogen Maxbac Manual): the DmLGIC cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, 1990, *Nuc. Acid. Res.* 18: 5667] into Sf9-cells. Recombinant pAC360 viruses are identified by the absence of inclusion bodies in infected cells and recombinant pBlueBac viruses are identified on the basis of b-galactosidase expression (Summers, M. D. and Smith, G. E., Texas Agriculture Exp. Station Bulletin No. 1555). Following plaque purification, DmLGIC expression is measured by the assays described herein.

The cDNA encoding the entire open reading frame for DmLGIC is inserted into the BamHI site of pBlueBacII. Constructs in the positive orientation are identified by sequence analysis and used to transfect Sf9 cells in the presence of linear AcNPV mild type DNA.

Authentic, active DmLGIC is found in the cytoplasm of infected cells. Active DmLGIC is extracted from infected cells by hypotonic or detergent lysis.

EXAMPLE 5

Cloning of DmLGIC cDNA into a Yeast Expression Vector

Recombinant DmLGIC is produced in the yeast *S. cerevisiae* following the insertion of the optimal DmLGIC cDNA cistron into expression vectors designed to direct the intracellular or extracellular expression of heterologous proteins. In the case of intracellular expression, vectors such as EmBLyex4 or the like are ligated to the DmLGIC cistron [Rinas, et al., 1990, *Biotechnology* 8: 543–545; Horowitz B. et al., 1989, *J. Biol. Chem.* 265: 4189–4192]. For extracellular expression, the DmLGIC cistron is ligated into yeast expression vectors which fuse a secretion signal (a yeast or mammalian peptide) to the $NH_2$ terminus of the DmLGIC protein [Jacobson, 1989, *Gene* 85: 511–516; Riett and Bellon, 1989, *Biochem.* 28: 2941–2949].

These vectors include, but are not limited to pAVE1-6, which fuses the human serum albumin signal to the expressed cDNA [Steep, 1990, *Biotechnology* 8: 42–46], and the vector pL8PL which fuses the human lysozyme signal to the expressed cDNA [Yamamoto, *Biochem.* 28: 2728–2732)]. In addition, DmLGIC is expressed in yeast as a fusion protein conjugated to ubiquitin utilizing the vector pVEP [Ecker, 1989, *J. Biol. Chem.* 264: 7715–7719, Sabin, 1989 *Biotechnology* 7: 705–709, McDonnell, 1989, *Mol. Cell Biol.* 9: 5517–5523 (1989)]. The levels of expressed DmLGIC are determined by the assays described herein.

EXAMPLE 6

Purification of Recombinant DmLGIC

Recombinantly produced DmLGIC may be purified by antibody affinity chromatography. DmLGIC antibody affinity columns are made by adding the anti-DmLGIC antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized DmLGIC are slowly passed through the column. The column is then washed with phosphate-buffered saline together with detergents until the optical density (A280) falls to background, then the protein is eluted with 0.23 M glycine-HCl (pH 2.6) together with detergents. The purified DmLGIC protein is then dialyzed against phosphate buffered saline.

EXAMPLE 7

Purification of Recombinant DmLGIC

According to the *Drosophila* genome sequencing project, Ac007815 [Ac15] and Ac007805 [Ac05] map to chromosome III; specifically Ac15 to ChIII 92B and Ac05 to ChIII 87B. DrosGluClalpha1 (glc-1), maps to ChIII 92B, as does Ac15. O'Tousa et al. (1989, *J. Neurogenetics* 6: 41–52) map photoreceptor mutations to the ChIII 92B region of the *Droshphila* genome. In addition, Stuart (1999, *Neuron* 22:431–433) notes that histamine is a potential invertebrate retinal neurotransmitter. Therefore, the data generated in Example section 2 herein in combination with the chromosomal location of Ac15 suggests that the LGIC disclosed herein are at least partially effective as being responsive to histamine.

What is claimed is:

1. A purified nucleic acid molecule encoding a *Drosophila* ligand-gated ion channel (LGIC) protein, wherein said protein comprises the amino acid sequence as set forth in SEQ ID NO:2.

2. An expression vector for expressing a *Drosophila* LGIC protein in a recombinant and isolated host cell wherein said expression vector comprises a DNA molecule of claim 1.

3. An isolated host cell which expresses a recombinant *Drosophila* LGIC protein wherein said host cell contains the expression vector of claim 2.

4. A process for expressing a *Drosophila* LGIC protein in a recombinant and isolated host cell, comprising:
   (a) transfecting the expression vector of claim 2 into a suitable host cell; and,
   (b) culturing the host cells of step (a) under conditions which allow expression of said *Drosophila* LGIC protein from said expression vector.

5. A purified DNA molecule encoding a *Drosophila* ligand-gated ion channel (LGIC) protein which comprises the nucleotide sequence as set forth in SEQ ID NO:1.

6. The DNA molecule of claim 5 containing from about nucleotide 199 to about nucleotide 1479 of SEQ ID NO:1.

7. A purified nucleic acid molecule encoding a *Drosophila* ligand-gated ion channel (LGIC) protein, wherein said protein comprises the amino acid sequence as set forth in SEQ ID NO:4.

8. An expression vector for expressing a *Drosophila* LGIC protein in a recombinant and isolated host cell wherein said expression vector comprises a DNA molecule of claim 7.

9. An isolated host cell which expresses a recombinant *Drosophila* LGIC protein wherein said host cell contains the expression vector of claim 8.

10. A process for expressing a *Drosophila* LGIC protein in a recombinant and isolated host cell, comprising:
   (a) transfecting the expression vector of claim 8 into a suitable host cell; and, (b) culturing the host cells of step (a) under conditions which allow expression of said *Drosophila* LGIC protein from said expression vector.

11. A purified DNA molecule encoding a *Drosophila* ligand-gated ion channel (LGIC) protein which comprises the nucleotide sequence as set forth in SEQ ID NO:3.

12. The DNA molecule of claim 11 containing from about nucleotide 199 to about nucleotide 1467 of SEQ ID NO:3.

13. A *Drosophila* ligand-gated ion channel (LGIC) protein substantially free from other proteins which comprises the amino acid sequence as set forth in SEQ ID NO:2.

14. A *Drosophila* LGIC protein of claim 13 which is a product of a DNA expression vector contained within a recombinant and isolated host cell.

15. A substantially pure membrane preparation comprising the *Drosophila* LGIC protein purified from the recombinant host cell of claim 14.

16. A *Drosophila* ligand-gated ion channel (LGIC) protein substantially free from other proteins which comprises the amino acid sequence as set forth in SEQ ID NO:4.

17. A *Drosophila* LGIC protein of claim 16 which is a product of a DNA expression vector contained within a recombinant and isolated host cell.

18. A substantially pure membrane preparation comprising the *Drosophila* LGIC protein purified from the recombinant host cell of claim 17.

19. A *Drosophila* ligand-gated ion channel (LGIC) protein substantially free from other proteins which consists of the amino acid sequence selected from the group consisting of amino acid sequences as set forth in SEQ ID NO:2 and SEQ ID NO:4.

20. A *Drosophila* ligand-gated ion channel (LGIC) homomultimer channel receptor substantially free from other proteins which comprises the amino acid sequence selected from the group consisting of SEQ ID NO:2 and SEQ ID NO:4.

21. A *Drosophila* LGIC protein of claim 20 which is a product of a DNA expression vector contained within a recombinant and isolated host cell.

22. A substantially pure membrane preparation comprising the *Drosophila* LGIC channel purified from the recombinant host cell of claim 21.

23. A *Drosophila* ligand-gated ion channel (LGIC) heteromultimer channel receptor substantially free from other proteins which comprises the amino acid sequence selected from the group consisting of SEQ ID NO:2 and SEQ ID NO:4.

24. A *Drosophila* LGIC protein of claim 23 which is a product of a DNA expression vector contained within a recombinant and isolated host cell.

25. A substantially pure membrane preparation comprising the *Drosophila* LGIC channel purified from the recombinant host cell of claim 24.

26. A method of identifying a modulator of a ligand-gated ion channel (LGIC) protein, comprising:

(a) contacting a labeled ligand of a *Drosophila* LGIC protein selected from the group consisting of SEQ ID NO:2 and SEQ ID NO:4 in the presence and absence of a test compound; and, (b) measuring the binding of the labeled ligand to the LGIC protein; wherein if the amount of binding of the labeled ligand is less in the presence of the test compound than in the absence of the test compound, the test compound is a potential modulator of the LGIC.

27. The method of claim 26 wherein the *Drosophila* LGIC protein of step (a) is a product of a DNA expression vector contained within a recombinant and isolated host cell.

* * * * *

SEQUENCE LISTING

<160> NUMBER OF SEQ ID NOS: 33

<210> SEQ ID NO 1
<211> LENGTH: 1518
<212> TYPE: DNA
<213> ORGANISM: Drosophila Melanogaster
<220> FEATURE:
<221> NAME/KEY: CDS
<222> LOCATION: (199)...(1479)

<400> SEQUENCE: 1

```
caatcgtcgc gataactctg ccgtttcttt attggttttt gctgcgcgac gagtaaaata      60
taattcctcg cttactaatc ctccgagcaa gttcattctc aagcgcaccc agagatgagc     120
tactttggga attgacatgg actgcggagc aatgagtgcc agaggaacaa tatcaaagcc     180
gaaggtagtg tgttcata atg caa agc cca act agc aaa ttg gta gaa ttc       231
                    Met Gln Ser Pro Thr Ser Lys Leu Val Glu Phe
                     1               5                  10 agg tgc ctt att gcg ttg gca ata tat ttg cac gcg ctg gag caa tcg       279
Arg Cys Leu Ile Ala Leu Ala Ile Tyr Leu His Ala Leu Glu Gln Ser
            15                  20                  25 atc cag cac tgc cat tgt gtt cat ggt tac aga aat aac acg gag agc       327
Ile Gln His Cys His Cys Val His Gly Tyr Arg Asn Asn Thr Glu Ser
        30                  35                  40 gcc gag ctg gtc tcc cac tac gag tcg agt ctt tcg ctc ccg gac att       375
Ala Glu Leu Val Ser His Tyr Glu Ser Ser Leu Ser Leu Pro Asp Ile
    45                  50                  55 ttg ccc att ccc tca aag acg tac gac aag aac cgg gct ccc aag ctc       423
Leu Pro Ile Pro Ser Lys Thr Tyr Asp Lys Asn Arg Ala Pro Lys Leu
60                  65                  70                  75 ctc ggc cag ccc aca gta gtc tac ttc cat gtc acg gtc ctc tcc ctg       471
Leu Gly Gln Pro Thr Val Val Tyr Phe His Val Thr Val Leu Ser Leu
                80                  85                  90 gac tcc att aac gag gag tct atg acc tat gtg acg gac atc ttc ctt       519
Asp Ser Ile Asn Glu Glu Ser Met Thr Tyr Val Thr Asp Ile Phe Leu
            95                 100                 105 gca caa agc tgg cgt gat cct cgc ctg cgg ttg cct gag aac atg agt       567
Ala Gln Ser Trp Arg Asp Pro Arg Leu Arg Leu Pro Glu Asn Met Ser
        110                 115                 120 gag cag tat cgc ata ttg gat gtc gac tgg ttg cac agc att tgg cgg       615
Glu Gln Tyr Arg Ile Leu Asp Val Asp Trp Leu His Ser Ile Trp Arg
    125                 130                 135 ccc gat tgc ttc ttt aag aac gcc aaa aag gtc acc ttc cat gag atg       663
Pro Asp Cys Phe Phe Lys Asn Ala Lys Lys Val Thr Phe His Glu Met
140                 145                 150                 155 agc att ccc aat cac tat ctc tgg ctg tac cac gac aaa acg ctg ctc       711
Ser Ile Pro Asn His Tyr Leu Trp Leu Tyr His Asp Lys Thr Leu Leu
                160                 165                 170 tat atg tcc aaa ctc acg ttg gtc ctg tcg tgc gcc atg aag ttt gag       759
Tyr Met Ser Lys Leu Thr Leu Val Leu Ser Cys Ala Met Lys Phe Glu
            175                 180                 185 tcc tat ccg cat gac acg caa atc tgc tcc atg atg atc gag agt tta       807
Ser Tyr Pro His Asp Thr Gln Ile Cys Ser Met Met Ile Glu Ser Leu
        190                 195                 200 tcc cat acg gtg gaa gat ttg gtt ttc att tgg aac atg acc gac cca       855
Ser His Thr Val Glu Asp Leu Val Phe Ile Trp Asn Met Thr Asp Pro
    205                 210                 215 ctt gtg gtt aac acg gag att gag ttg ccg cag cta gac ata tca aat       903
Leu Val Val Asn Thr Glu Ile Glu Leu Pro Gln Leu Asp Ile Ser Asn
```

```
                220                 225                 230                 235
aac tac aca acc gac tgt act ata gag tac tca aca ggt aac ttc acc         951
Asn Tyr Thr Thr Asp Cys Thr Ile Glu Tyr Ser Thr Gly Asn Phe Thr
                240                 245                 250 tgc ctg gcc att gtg ttc aac ctg cgc cga cgc ctg ggt tac cat ttg         999
Cys Leu Ala Ile Val Phe Asn Leu Arg Arg Arg Leu Gly Tyr His Leu
                    255                 260                 265 ttc cac acc tac atc ccc tcg gct ctg att gtg gtc atg tct tgg ata        1047
Phe His Thr Tyr Ile Pro Ser Ala Leu Ile Val Val Met Ser Trp Ile
                270                 275                 280 tcg ttt tgg ata aaa cca gaa gcg ata ccc gcc cgt gta act ctg gga        1095
Ser Phe Trp Ile Lys Pro Glu Ala Ile Pro Ala Arg Val Thr Leu Gly
            285                 290                 295 gtg acc tca ctg cta acc ctg gcc acc cag aat acc cag tcg caa caa        1143
Val Thr Ser Leu Leu Thr Leu Ala Thr Gln Asn Thr Gln Ser Gln Gln
300                 305                 310                 315 tcg ctg ccg ccg gtt tcg tat gtc aag gct ata gac gtc tgg atg tcg        1191
Ser Leu Pro Pro Val Ser Tyr Val Lys Ala Ile Asp Val Trp Met Ser
                320                 325                 330 tcc tgt tcg gtg ttt gta ttc ctt tct ctg atg gaa ttt gca gtg gtc        1239
Ser Cys Ser Val Phe Val Phe Leu Ser Leu Met Glu Phe Ala Val Val
                335                 340                 345 aac aat ttt atg gga ccg gtg gcc aca aag gca atg aag ggg tat tcg        1287
Asn Asn Phe Met Gly Pro Val Ala Thr Lys Ala Met Lys Gly Tyr Ser
            350                 355                 360 gac gag aac atc agt gat ctg gac gac cta aag tct gca cta cag cat        1335
Asp Glu Asn Ile Ser Asp Leu Asp Asp Leu Lys Ser Ala Leu Gln His
365                 370                 375 cat cgg gaa tcg att att gag ccc cag tac gac act ttc tgc cat ggc        1383
His Arg Glu Ser Ile Ile Glu Pro Gln Tyr Asp Thr Phe Cys His Gly
380                 385                 390                 395 cat gcc aca gcc att tat ata gac aaa ttc tcg cgc ttt ttc ttc ccg        1431
His Ala Thr Ala Ile Tyr Ile Asp Lys Phe Ser Arg Phe Phe Phe Pro
                400                 405                 410 ttt tcg ttc ttt ata ctc aat att gtc tat tgg aca acg ttc cta tga        1479
Phe Ser Phe Phe Ile Leu Asn Ile Val Tyr Trp Thr Thr Phe Leu *
            415                 420                 425 tggatggaaa agtttctccg aaggaataga gcgtaaaca                              1518

<210> SEQ ID NO 2
<211> LENGTH: 426
<212> TYPE: PRT
<213> ORGANISM: Drosophila Melanogaster

<400> SEQUENCE: 2

Met Gln Ser Pro Thr Ser Lys Leu Val Glu Phe Arg Cys Leu Ile Ala
1               5                   10                  15

Leu Ala Ile Tyr Leu His Ala Leu Glu Gln Ser Ile Gln His Cys His
                20                  25                  30

Cys Val His Gly Tyr Arg Asn Asn Thr Glu Ser Ala Glu Leu Val Ser
            35                  40                  45

His Tyr Glu Ser Ser Leu Ser Leu Pro Asp Ile Leu Pro Ile Pro Ser
        50                  55                  60

Lys Thr Tyr Asp Lys Asn Arg Ala Pro Lys Leu Leu Gly Gln Pro Thr
65                  70                  75                  80

Val Val Tyr Phe His Val Thr Val Leu Ser Leu Asp Ser Ile Asn Glu
                85                  90                  95

Glu Ser Met Thr Tyr Val Thr Asp Ile Phe Leu Ala Gln Ser Trp Arg
```

-continued

```
                    100                 105                 110
Asp Pro Arg Leu Arg Leu Pro Glu Asn Met Ser Glu Gln Tyr Arg Ile
            115                 120                 125
Leu Asp Val Asp Trp Leu His Ser Ile Trp Arg Pro Asp Cys Phe Phe
        130                 135                 140
Lys Asn Ala Lys Lys Val Thr Phe His Glu Met Ser Ile Pro Asn His
145                 150                 155                 160
Tyr Leu Trp Leu Tyr His Asp Lys Thr Leu Leu Tyr Met Ser Lys Leu
                165                 170                 175
Thr Leu Val Leu Ser Cys Ala Met Lys Phe Glu Ser Tyr Pro His Asp
            180                 185                 190
Thr Gln Ile Cys Ser Met Met Ile Glu Ser Leu Ser His Thr Val Glu
        195                 200                 205
Asp Leu Val Phe Ile Trp Asn Met Thr Asp Pro Leu Val Val Asn Thr
    210                 215                 220
Glu Ile Glu Leu Pro Gln Leu Asp Ile Ser Asn Asn Tyr Thr Thr Asp
225                 230                 235                 240
Cys Thr Ile Glu Tyr Ser Thr Gly Asn Phe Thr Cys Leu Ala Ile Val
                245                 250                 255
Phe Asn Leu Arg Arg Arg Leu Gly Tyr His Leu Phe His Thr Tyr Ile
            260                 265                 270
Pro Ser Ala Leu Ile Val Val Met Ser Trp Ile Ser Phe Trp Ile Lys
        275                 280                 285
Pro Glu Ala Ile Pro Ala Arg Val Thr Leu Gly Val Thr Ser Leu Leu
    290                 295                 300
Thr Leu Ala Thr Gln Asn Thr Gln Ser Gln Gln Ser Leu Pro Pro Val
305                 310                 315                 320
Ser Tyr Val Lys Ala Ile Asp Val Trp Met Ser Ser Cys Ser Val Phe
                325                 330                 335
Val Phe Leu Ser Leu Met Glu Phe Ala Val Val Asn Asn Phe Met Gly
            340                 345                 350
Pro Val Ala Thr Lys Ala Met Lys Gly Tyr Ser Asp Glu Asn Ile Ser
        355                 360                 365
Asp Leu Asp Asp Leu Lys Ser Ala Leu Gln His His Arg Glu Ser Ile
    370                 375                 380
Ile Glu Pro Gln Tyr Asp Thr Phe Cys His Gly His Ala Thr Ala Ile
385                 390                 395                 400
Tyr Ile Asp Lys Phe Ser Arg Phe Phe Phe Pro Phe Ser Phe Phe Ile
                405                 410                 415
Leu Asn Ile Val Tyr Trp Thr Thr Phe Leu
            420                 425
```

<210> SEQ ID NO 3
<211> LENGTH: 1506
<212> TYPE: DNA
<213> ORGANISM: Drosophila Melanogaster
<220> FEATURE:
<221> NAME/KEY: CDS
<222> LOCATION: (199)...(1467)

<400> SEQUENCE: 3

```
caatcgtcgc gataactctg ccgtttcttt attggttttt gctgcgcgac gagtaaaata    60
taattcctcg cttactaatc ctccgagcaa gttcattctc aagcgcaccc agagatgagc   120
tactttggga attgacatgg actgcggagc aatgagtgcc agaggaacaa tatcaaagcc   180
```

```
gaaggtagtg tgttcata atg caa agc cca act agc aaa ttg gta gaa ttc      231
               Met Gln Ser Pro Thr Ser Lys Leu Val Glu Phe
                1               5                  10 agg tgc ctt att gcg ttg gca ata tat ttg cac gcg ctg gag caa tcg      279
Arg Cys Leu Ile Ala Leu Ala Ile Tyr Leu His Ala Leu Glu Gln Ser
             15                  20                  25 atc cag cac tgc cat tgt gtt cat ggt tac aga aat aac acg gag agc      327
Ile Gln His Cys His Cys Val His Gly Tyr Arg Asn Asn Thr Glu Ser
         30                  35                  40 gcc gag ctg gtc tcc cac tac gag tcg agt ctt tcg ctc ccg gac att      375
Ala Glu Leu Val Ser His Tyr Glu Ser Ser Leu Ser Leu Pro Asp Ile
     45                  50                  55 ttg ccc att ccc tca aag acg tac gac aag aac cgg gct ccc aag ctc      423
Leu Pro Ile Pro Ser Lys Thr Tyr Asp Lys Asn Arg Ala Pro Lys Leu
 60                  65                  70                  75 ctc ggc cag ccc aca gta gtc tac ttc cat gtc acg gtc ctc tcc ctg      471
Leu Gly Gln Pro Thr Val Val Tyr Phe His Val Thr Val Leu Ser Leu
                 80                  85                  90 gac tcc att aac gag gag tct atg acc tat gtg acg gac atc ttc ctt      519
Asp Ser Ile Asn Glu Glu Ser Met Thr Tyr Val Thr Asp Ile Phe Leu
             95                 100                 105 gca caa agc tgg cgt gat cct cgc ctg cgg ttg cct gag aac atg agt      567
Ala Gln Ser Trp Arg Asp Pro Arg Leu Arg Leu Pro Glu Asn Met Ser
         110                 115                 120 gag cag tat cgc ata ttg gat gtc gac tgg ttg cac agc att tgg cgg      615
Glu Gln Tyr Arg Ile Leu Asp Val Asp Trp Leu His Ser Ile Trp Arg
     125                 130                 135 ccc gat tgc ttc ttt aag aac gcc aaa aag gtc acc ttc cat gag atg      663
Pro Asp Cys Phe Phe Lys Asn Ala Lys Lys Val Thr Phe His Glu Met
140                 145                 150                 155 agc att ccc aat cac tat ctc tgg ctg tac cac gac aaa acg ctg ctc      711
Ser Ile Pro Asn His Tyr Leu Trp Leu Tyr His Asp Lys Thr Leu Leu
             160                 165                 170 tat atg tcc aaa ctc acg ttg gtc ctg tcg tgc gcc atg aag ttt gag      759
Tyr Met Ser Lys Leu Thr Leu Val Leu Ser Cys Ala Met Lys Phe Glu
         175                 180                 185 tcc tat ccg cat gac acg caa atc tgc tcc atg atg atc gag agt tta      807
Ser Tyr Pro His Asp Thr Gln Ile Cys Ser Met Met Ile Glu Ser Leu
     190                 195                 200 tcc cat acg gtg gaa gat ttg gtt ttc att tgg aac atg acc gac cca      855
Ser His Thr Val Glu Asp Leu Val Phe Ile Trp Asn Met Thr Asp Pro
205                 210                 215 ctt gtg gtt aac acg gag att gag ttg ccg cag cta gac ata tca aat      903
Leu Val Val Asn Thr Glu Ile Glu Leu Pro Gln Leu Asp Ile Ser Asn
220                 225                 230                 235 aac tac aca acc gac tgt act ata gag tac tca aca ggt aac ttc acc      951
Asn Tyr Thr Thr Asp Cys Thr Ile Glu Tyr Ser Thr Gly Asn Phe Thr
             240                 245                 250 tgc ctg gcc att gtg ttc aac ctg cgc cga cgc ctg ggt tac cat ttg      999
Cys Leu Ala Ile Val Phe Asn Leu Arg Arg Arg Leu Gly Tyr His Leu
         255                 260                 265 ttc cac acc tac atc ccc tcg gct ctg att gtg gtc atg tct tgg ata     1047
Phe His Thr Tyr Ile Pro Ser Ala Leu Ile Val Val Met Ser Trp Ile
     270                 275                 280 tcg ttt tgg ata aaa cca gaa gcg ata ccc gcc cgt gta act ctg gga     1095
Ser Phe Trp Ile Lys Pro Glu Ala Ile Pro Ala Arg Val Thr Leu Gly
285                 290                 295 gtg acc tca ctg cta acc ctg gcc acc cag aat acc cag tcg caa caa     1143
Val Thr Ser Leu Leu Thr Leu Ala Thr Gln Asn Thr Gln Ser Gln Gln
300                 305                 310                 315
```

```
tcg ctg ccg ccg gtt tcg tat gtc aag gct ata gac gtc tgg atg tcg      1191
Ser Leu Pro Pro Val Ser Tyr Val Lys Ala Ile Asp Val Trp Met Ser
            320                 325                 330 tcc tgt tcg gtg ttt gta ttc ctt tct ctg atg gaa ttt gca gtg gtc      1239
Ser Cys Ser Val Phe Val Phe Leu Ser Leu Met Glu Phe Ala Val Val
        335                 340                 345 aac aat ttt atg gga ccg gtg gcc aca aag gca atg aag ggg tat tcg      1287
Asn Asn Phe Met Gly Pro Val Ala Thr Lys Ala Met Lys Gly Tyr Ser
    350                 355                 360 gac gag aac atc agt gat ctg gac gac cta aag cat cat cgg gaa tcg      1335
Asp Glu Asn Ile Ser Asp Leu Asp Asp Leu Lys His His Arg Glu Ser
365                 370                 375 att att gag ccc cag tac gac act ttc tgc cat ggc cat gcc aca gcc      1383
Ile Ile Glu Pro Gln Tyr Asp Thr Phe Cys His Gly His Ala Thr Ala
380                 385                 390                 395 att tat ata gac aaa ttc tcg cgc ttt ttc ttc ccg ttt tcg ttc ttt      1431
Ile Tyr Ile Asp Lys Phe Ser Arg Phe Phe Phe Pro Phe Ser Phe Phe
                400                 405                 410 ata ctc aat att gtc tat tgg aca acg ttc cta tga tggatggaaa           1477
Ile Leu Asn Ile Val Tyr Trp Thr Thr Phe Leu *
            415                 420 agtttctccg aaggaataga gcgtaaaca                                       1506

<210> SEQ ID NO 4
<211> LENGTH: 422
<212> TYPE: PRT
<213> ORGANISM: Drosophila Melanogaster

<400> SEQUENCE: 4

Met Gln Ser Pro Thr Ser Lys Leu Val Glu Phe Arg Cys Leu Ile Ala
1               5                   10                  15

Leu Ala Ile Tyr Leu His Ala Leu Glu Gln Ser Ile Gln His Cys His
            20                  25                  30

Cys Val His Gly Tyr Arg Asn Asn Thr Glu Ser Ala Glu Leu Val Ser
        35                  40                  45

His Tyr Glu Ser Ser Leu Ser Leu Pro Asp Ile Leu Pro Ile Pro Ser
    50                  55                  60

Lys Thr Tyr Asp Lys Asn Arg Ala Pro Lys Leu Leu Gly Gln Pro Thr
65                  70                  75                  80

Val Val Tyr Phe His Val Thr Val Leu Ser Leu Asp Ser Ile Asn Glu
                85                  90                  95

Glu Ser Met Thr Tyr Val Thr Asp Ile Phe Leu Ala Gln Ser Trp Arg
            100                 105                 110

Asp Pro Arg Leu Arg Leu Pro Glu Asn Met Ser Glu Gln Tyr Arg Ile
        115                 120                 125

Leu Asp Val Asp Trp Leu His Ser Ile Trp Arg Pro Asp Cys Phe Phe
    130                 135                 140

Lys Asn Ala Lys Lys Val Thr Phe His Glu Met Ser Ile Pro Asn His
145                 150                 155                 160

Tyr Leu Trp Leu Tyr His Asp Lys Thr Leu Tyr Met Ser Lys Leu
                165                 170                 175

Thr Leu Val Leu Ser Cys Ala Met Lys Phe Glu Ser Tyr Pro His Asp
            180                 185                 190

Thr Gln Ile Cys Ser Met Met Ile Glu Ser Leu Ser His Thr Val Glu
        195                 200                 205

Asp Leu Val Phe Ile Trp Asn Met Thr Asp Pro Leu Val Val Asn Thr
```

-continued

```
              210                 215                 220
Glu Ile Glu Leu Pro Gln Leu Asp Ile Ser Asn Asn Tyr Thr Thr Asp
225                 230                 235                 240
Cys Thr Ile Glu Tyr Ser Thr Gly Asn Phe Thr Cys Leu Ala Ile Val
                245                 250                 255
Phe Asn Leu Arg Arg Arg Leu Gly Tyr His Leu Phe His Thr Tyr Ile
                260                 265                 270
Pro Ser Ala Leu Ile Val Val Met Ser Trp Ile Ser Phe Trp Ile Lys
                275                 280                 285
Pro Glu Ala Ile Pro Ala Arg Val Thr Leu Gly Val Thr Ser Leu Leu
                290                 295                 300
Thr Leu Ala Thr Gln Asn Thr Gln Ser Gln Gln Ser Leu Pro Pro Val
305                 310                 315                 320
Ser Tyr Val Lys Ala Ile Asp Val Trp Met Ser Ser Cys Ser Val Phe
                325                 330                 335
Val Phe Leu Ser Leu Met Glu Phe Ala Val Val Asn Asn Phe Met Gly
                340                 345                 350
Pro Val Ala Thr Lys Ala Met Lys Gly Tyr Ser Asp Glu Asn Ile Ser
                355                 360                 365
Asp Leu Asp Asp Leu Lys His His Arg Glu Ser Ile Ile Glu Pro Gln
                370                 375                 380
Tyr Asp Thr Phe Cys His Gly His Ala Thr Ala Ile Tyr Ile Asp Lys
385                 390                 395                 400
Phe Ser Arg Phe Phe Pro Phe Ser Phe Phe Ile Leu Asn Ile Val
                405                 410                 415
Tyr Trp Thr Thr Phe Leu
                420

<210> SEQ ID NO 5
<211> LENGTH: 2073
<212> TYPE: DNA
<213> ORGANISM: Drosophila Melanogaster
<220> FEATURE:
<221> NAME/KEY: CDS
<222> LOCATION: (330)...(1787)

<400> SEQUENCE: 5
aactgccaag acgtttagaa cggaaaaact gaattttcaa aaatatttcg agtaaactgt      60
taaatgctga agtgttctga atattccctt aaaacataga aaccttcttt gacatcttta     120
taaagcaata aaattcattc gggaagttta tgaatagtgg tgttattaat catgccattt     180
gtggcgtcaa gctgatggtt atgtaatctc tgtgaagatt ctagaaatcc aacagaaata     240
tattgcttcg aaaccaagc aaagattact tgactggaga ggaaagctat ttcgaattca      300
tctaaaaact gtaaagagtt cacattaaa atg gtg ttc caa ata ata atc ctg      353
                                   Met Val Phe Gln Ile Ile Ile Leu
                                     1               5 gtg atc tgc acc atc tgc atg aag cac tac gcc aaa ggg gag ttt caa     401
Val Ile Cys Thr Ile Cys Met Lys His Tyr Ala Lys Gly Glu Phe Gln
     10                  15                  20 caa agt ctg gcc ata acc gac atc ctg ccc gag gac atc aag cgt tac     449
Gln Ser Leu Ala Ile Thr Asp Ile Leu Pro Glu Asp Ile Lys Arg Tyr
 25                  30                  35                  40 gac aag atg aga ccg ccg aag aaa gag ggt cag ccg acg ata gtc tac     497
Asp Lys Met Arg Pro Pro Lys Lys Glu Gly Gln Pro Thr Ile Val Tyr
                 45                  50                  55 ttc cat gtg act gtg atg ggt ctg gac tcc att gat gag aac tcg atg     545
Phe His Val Thr Val Met Gly Leu Asp Ser Ile Asp Glu Asn Ser Met
```

```
                Phe His Val Thr Val Met Gly Leu Asp Ser Ile Asp Glu Asn Ser Met
                             60                  65                  70 act tat gtg gcg gat gtg ttc ttt gca cag acg tgg aag gat cat cgc            593
Thr Tyr Val Ala Asp Val Phe Phe Ala Gln Thr Trp Lys Asp His Arg
             75                  80                  85 ctg cga ttg ccg gag aat atg aca cag gaa tac cgc ctg ctc gag gtg            641
Leu Arg Leu Pro Glu Asn Met Thr Gln Glu Tyr Arg Leu Leu Glu Val
         90                  95                 100 gac tgg cta aaa aat atg tgg cgc ccg gat tcg ttt ttc aaa aac gcc            689
Asp Trp Leu Lys Asn Met Trp Arg Pro Asp Ser Phe Phe Lys Asn Ala
105                 110                 115                 120 aaa tcg gtg acc ttt cag acc atg aca ata ccc aat cac tat atg tgg            737
Lys Ser Val Thr Phe Gln Thr Met Thr Ile Pro Asn His Tyr Met Trp
                125                 130                 135 ctg tac aag gat aag acc att ctc tat atg gtc aag cta aca ctg aag            785
Leu Tyr Lys Asp Lys Thr Ile Leu Tyr Met Val Lys Leu Thr Leu Lys
            140                 145                 150 ctg tcc tgc atc atg aat ttc gcc att tat cct cat gac aca cag gag            833
Leu Ser Cys Ile Met Asn Phe Ala Ile Tyr Pro His Asp Thr Gln Glu
        155                 160                 165 tgc aag ctg caa atg gaa agc ctg tcc cac acc acg gat gac ttg ata            881
Cys Lys Leu Gln Met Glu Ser Leu Ser His Thr Thr Asp Asp Leu Ile
    170                 175                 180 ttc cag tgg gat cca aca acg ccc ctt gtg gtt gat gaa aac atc gaa            929
Phe Gln Trp Asp Pro Thr Thr Pro Leu Val Val Asp Glu Asn Ile Glu
185                 190                 195                 200 ctg ccg cag gtg gcc ctc atc cgg aat gaa acg gcg gac tgc acc cag            977
Leu Pro Gln Val Ala Leu Ile Arg Asn Glu Thr Ala Asp Cys Thr Gln
                205                 210                 215 gtt tat tcc act ggc aac ttc aca tgc ctg gag gtg gtg ttc acc ctt           1025
Val Tyr Ser Thr Gly Asn Phe Thr Cys Leu Glu Val Val Phe Thr Leu
            220                 225                 230 aag cgt cgt ttg gtt tac tac gtt ttc aac acc tac att ccc acc tgc           1073
Lys Arg Arg Leu Val Tyr Tyr Val Phe Asn Thr Tyr Ile Pro Thr Cys
        235                 240                 245 atg ata gtg atc atg tca tgg gta tcc ttc tgg atc aaa ccg gag gcg           1121
Met Ile Val Ile Met Ser Trp Val Ser Phe Trp Ile Lys Pro Glu Ala
    250                 255                 260 gca cca gcc cgt gtg act ctg ggt gtc acc tcc ttg cta acg ctt tcc           1169
Ala Pro Ala Arg Val Thr Leu Gly Val Thr Ser Leu Leu Thr Leu Ser
265                 270                 275                 280 acg caa cac gcc aaa tcg cag tcg tct ttg cca cct gtt tcc tat ctc           1217
Thr Gln His Ala Lys Ser Gln Ser Ser Leu Pro Pro Val Ser Tyr Leu
                285                 290                 295 aag gca gtg gac gcc ttt atg tcc gtt tgc acg gtg ttc gtg ttt atg           1265
Lys Ala Val Asp Ala Phe Met Ser Val Cys Thr Val Phe Val Phe Met
            300                 305                 310 gcc ctc atg gag tat tgt cta ata aac atc gtc ctg agc gac acg ccc           1313
Ala Leu Met Glu Tyr Cys Leu Ile Asn Ile Val Leu Ser Asp Thr Pro
        315                 320                 325 att ccc aag ccg atg gct tat cca ccc aaa cct gtg gcg ggc gat ggg           1361
Ile Pro Lys Pro Met Ala Tyr Pro Pro Lys Pro Val Ala Gly Asp Gly
    330                 335                 340 ccc aag aaa gag ggc gag ggt gct cct cct ggg ggc agc aac tcg acg           1409
Pro Lys Lys Glu Gly Glu Gly Ala Pro Pro Gly Gly Ser Asn Ser Thr
345                 350                 355                 360 gcc agc aag caa caa gcc acc atg ttg cca ctg gcc gat gaa aag atc           1457
Ala Ser Lys Gln Gln Ala Thr Met Leu Pro Leu Ala Asp Glu Lys Ile
                365                 370                 375
```

-continued

| | | |
|---|---|---|
| gag aaa att gag aag atc ttt gac gag atg acc aag aat aga agg att<br>Glu Lys Ile Glu Lys Ile Phe Asp Glu Met Thr Lys Asn Arg Arg Ile<br>380 385 390 | | 1505 |
| gta acc acc aca cgc cgc gtg gtg cgt cca cca ttg gac gcc gat ggt<br>Val Thr Thr Thr Arg Arg Val Val Arg Pro Pro Leu Asp Ala Asp Gly<br>395 400 405 | | 1553 |
| ccg tgg att ccg cga cag gag tcg cgg ata ata ctg acc ccg act atc<br>Pro Trp Ile Pro Arg Gln Glu Ser Arg Ile Ile Leu Thr Pro Thr Ile<br>410 415 420 | | 1601 |
| gct ccg ccg cca ccg ccc cct cag cca gcg gca ccg gaa ccg gaa cta<br>Ala Pro Pro Pro Pro Pro Gln Pro Ala Ala Pro Glu Pro Glu Leu<br>425 430 435 440 | | 1649 |
| ccc aag ccg aaa ctc aca ccc gcc cag gag cgg ctc aag cgg gct ata<br>Pro Lys Pro Lys Leu Thr Pro Ala Gln Glu Arg Leu Lys Arg Ala Ile<br>445 450 455 | | 1697 |
| tat ata gat cgg tcc tcg cgc gtc ctt ttc ccc gcc ctc ttc gcc agt<br>Tyr Ile Asp Arg Ser Ser Arg Val Leu Phe Pro Ala Leu Phe Ala Ser<br>460 465 470 | | 1745 |
| ctg aat ggc atc tac tgg tgt gtg ttc tac gag tat cta taa<br>Leu Asn Gly Ile Tyr Trp Cys Val Phe Tyr Glu Tyr Leu *<br>475 480 485 | | 1787 |
| ggactacgac gactgtgccc tgtaaatact ttcgctagct ctctggcact ccatccgagt | | 1847 |
| gttaaacgtt gattgttcgc atatatcgaa acgtgtatcg caaatttaat cttaagcttt | | 1907 |
| cacgcacaag ctttaagtca atgaatttta aacatagatt attgttaaac cagaaggaag | | 1967 |
| gaataatggt acagatggag atctgattac aggataaatt acaaattatc aattcaattc | | 2027 |
| ctaaaatgct taaagttaat caagtgacgt agtagctgat gtagcc | | 2073 |

<210> SEQ ID NO 6
<211> LENGTH: 2034
<212> TYPE: DNA
<213> ORGANISM: Drosophila Melanogaster
<220> FEATURE:
<221> NAME/KEY: CDS
<222> LOCATION: (278)...(1735)

<400> SEQUENCE: 6

| | |
|---|---|
| cgagtaaact gttaaatgct gaagtgttct gaaatattcc ttaaaacata gaaaccttct | 60 |
| ttgacatctt tataaagcaa taaaattcat tcgggaagtt tatgaatagt ggtgttatta | 120 |
| atcatgccat ttgtggcgtc aagctgatgg ttatgtaatc tctgtgaaga ttctagaaat | 180 |
| ccaacagaaa tatattgctt cgaaaaccaa gcaaagatta cttgactgga gaggaaagct | 240 |
| atttcgaatt catctaaaaa ctgtagctca cattaaa atg gtg ttc caa ata ata<br>Met Val Phe Gln Ile Ile<br>1 5 | 295 |
| atc ctg gtg atc tgc acc atc tgc atg aag cac tac gcc aaa ggg gag<br>Ile Leu Val Ile Cys Thr Ile Cys Met Lys His Tyr Ala Lys Gly Glu<br>10 15 20 | 343 |
| ttt caa caa agt ctg gcc ata acc gac atc ctg ccc gag gac atc aag<br>Phe Gln Gln Ser Leu Ala Ile Thr Asp Ile Leu Pro Glu Asp Ile Lys<br>25 30 35 | 391 |
| cgt tac gac aag atg aga ccg ccg aag aaa gag ggt cag ccg acg ata<br>Arg Tyr Asp Lys Met Arg Pro Pro Lys Lys Glu Gly Gln Pro Thr Ile<br>40 45 50 | 439 |
| gtc tac ttc cat gtg act gtg atg ggt ctg gac tcc att gat gag aac<br>Val Tyr Phe His Val Thr Val Met Gly Leu Asp Ser Ile Asp Glu Asn<br>55 60 65 70 | 487 |
| tcg atg act tat gtg gcg gat gtg ttc ttt gca cag acg tgg aag gat<br>Ser Met Thr Tyr Val Ala Asp Val Phe Phe Ala Gln Thr Trp Lys Asp | 535 |

-continued

```
                          75                      80                      85
cat cgc ctg cga ttg ccg gag aat atg aca cag gaa tac cgc ctg ctc        583
His Arg Leu Arg Leu Pro Glu Asn Met Thr Gln Glu Tyr Arg Leu Leu
            90                      95                     100 gag gtg gac tgg cta aaa aat atg tgg cgg ccg gat tcg ttt ttc aaa        631
Glu Val Asp Trp Leu Lys Asn Met Trp Arg Pro Asp Ser Phe Phe Lys
           105                     110                     115 aac gcc aaa tcg gtg acc ttt cag acc atg aca ata ccc aat cac tat        679
Asn Ala Lys Ser Val Thr Phe Gln Thr Met Thr Ile Pro Asn His Tyr
       120                     125                     130 atg tgg ctg tac aag gat aag acc att ctg tac atg gtc aaa cta aca        727
Met Trp Leu Tyr Lys Asp Lys Thr Ile Leu Tyr Met Val Lys Leu Thr
135                     140                     145                     150 ctg aag ctg tcc tgc atc atg aac ttc gcc att tat cct cat gat aca        775
Leu Lys Leu Ser Cys Ile Met Asn Phe Ala Ile Tyr Pro His Asp Thr
               155                     160                     165 cag gag tgc aag ctg caa atg gaa agc ctg tcc cac acc acg gat gac        823
Gln Glu Cys Lys Leu Gln Met Glu Ser Leu Ser His Thr Thr Asp Asp
           170                     175                     180 ttg ata ttt cag tgg gat cca acg acg ccc ctt gtg gtt gat gaa aac        871
Leu Ile Phe Gln Trp Asp Pro Thr Thr Pro Leu Val Val Asp Glu Asn
       185                     190                     195 atc gag ctg ccg cag gtg gcc ctc atc cga aat gaa acg gcg gac tgt        919
Ile Glu Leu Pro Gln Val Ala Leu Ile Arg Asn Glu Thr Ala Asp Cys
   200                     205                     210 acc caa gtt tat tcc act ggc aac ttc aca tgc ctg gag gtg gtg ttc        967
Thr Gln Val Tyr Ser Thr Gly Asn Phe Thr Cys Leu Glu Val Val Phe
215                     220                     225                     230 acc ctt aag cgt cgt ttg gtt tac tac gtt ttc aac acc tac att ccc       1015
Thr Leu Lys Arg Arg Leu Val Tyr Tyr Val Phe Asn Thr Tyr Ile Pro
               235                     240                     245 acc tgc atg ata gtg atc atg tca tgg gta tcc ttc tgg atc aaa ccg       1063
Thr Cys Met Ile Val Ile Met Ser Trp Val Ser Phe Trp Ile Lys Pro
           250                     255                     260 gag gcg gca cca gcc cgt gtg act ctg ggt gtc acc tcc ttg cta acg       1111
Glu Ala Ala Pro Ala Arg Val Thr Leu Gly Val Thr Ser Leu Leu Thr
       265                     270                     275 ctt tcc acg caa cac gcc aaa tcg cag tcg tct ttg cca cct gtt tcc       1159
Leu Ser Thr Gln His Ala Lys Ser Gln Ser Ser Leu Pro Pro Val Ser
   280                     285                     290 tat ctc aag gca gtg gac gcc ttt atg tcc gtt tgc acg gtg ttc gtg       1207
Tyr Leu Lys Ala Val Asp Ala Phe Met Ser Val Cys Thr Val Phe Val
295                     300                     305                     310 ttt atg gcc ctc atg gag tat tgt cta ata aac atc gtc ctg agc gac       1255
Phe Met Ala Leu Met Glu Tyr Cys Leu Ile Asn Ile Val Leu Ser Asp
               315                     320                     325 acg ccc att ccc aag ccg atg gcc tat cca ccc aaa cct gtg gcg gga       1303
Thr Pro Ile Pro Lys Pro Met Ala Tyr Pro Pro Lys Pro Val Ala Gly
           330                     335                     340 gat ggg ccc aag aaa gag ggc gag ggt gct cct cct ggg ggc agc aac       1351
Asp Gly Pro Lys Lys Glu Gly Glu Gly Ala Pro Pro Gly Gly Ser Asn
       345                     350                     355 tcg acg gcc agc aag caa caa gcc acc atg ttg cca ctg gcc gat gaa       1399
Ser Thr Ala Ser Lys Gln Gln Ala Thr Met Leu Pro Leu Ala Asp Glu
   360                     365                     370 aag atc gag aaa att gag aag atc ttt gac gag atg acc aag aat aga       1447
Lys Ile Glu Lys Ile Glu Lys Ile Phe Asp Glu Met Thr Lys Asn Arg
375                     380                     385                     390 agg att gta acc acc aca cgc cgc gtg gtg cgt ccg cca ttg gac gcc       1495
Arg Ile Val Thr Thr Thr Arg Arg Val Val Arg Pro Pro Leu Asp Ala
```

-continued

```
Arg Ile Val Thr Thr Arg Arg Val Val Arg Pro Pro Leu Asp Ala
            395             400             405
gat ggt ccg tgg att ccg cga cag gag tcg cgg ata ata ctg acc ccg      1543
Asp Gly Pro Trp Ile Pro Arg Gln Glu Ser Arg Ile Ile Leu Thr Pro
            410             415             420
act atc gct ccg ccg cca ccg ccc cct cag cca gcg gca ccg gaa ccg      1591
Thr Ile Ala Pro Pro Pro Pro Pro Pro Gln Pro Ala Ala Pro Glu Pro
            425             430             435
gaa ctg ccc aag ccg aaa ctc aca ccc gcc cag gag cgg ctc aag cgg      1639
Glu Leu Pro Lys Pro Lys Leu Thr Pro Ala Gln Glu Arg Leu Lys Arg
            440             445             450
gct ata tat ata gat cgg tcc tcg cgc gtc ctt ttc ccc gcc ctc ttc      1687
Ala Ile Tyr Ile Asp Arg Ser Ser Arg Val Leu Phe Pro Ala Leu Phe
455             460             465             470
gcc agt ctg aat ggc atc tac tgg tgt gtg ttc tac gag tat cta taa      1735
Ala Ser Leu Asn Gly Ile Tyr Trp Cys Val Phe Tyr Glu Tyr Leu  *
            475             480             485 ggactacgac gactgtgccc tgtaaatact ttcgctagct ctctggcact ccatccgagt    1795
gttaaacgtt gattgttcgc atatatcgaa acgtgtatcg caaatttaat cttaagcttt    1855
cacgcacaag ctttaagtca atgaatttta aacatagatt attgttaaac cagaaggaag    1915
gaataatggt acagatggag atctgattac aggataaatt acaaattatc aattcaattc    1975
ctaaaatgct taagttaat caagtgacgt agtagctgat gtagcctaag tgaattgta      2034
```

<210> SEQ ID NO 7
<211> LENGTH: 485
<212> TYPE: PRT
<213> ORGANISM: Drosophila Melanogaster

<400> SEQUENCE: 7

```
Met Val Phe Gln Ile Ile Leu Val Ile Cys Thr Ile Cys Met Lys
 1               5                  10                  15

His Tyr Ala Lys Gly Glu Phe Gln Gln Ser Leu Ala Ile Thr Asp Ile
                20                  25                  30

Leu Pro Glu Asp Ile Lys Arg Tyr Asp Lys Met Arg Pro Pro Lys Lys
            35                  40                  45

Glu Gly Gln Pro Thr Ile Val Tyr Phe His Val Thr Val Met Gly Leu
        50                  55                  60

Asp Ser Ile Asp Glu Asn Ser Met Thr Tyr Val Ala Asp Val Phe Phe
65                  70                  75                  80

Ala Gln Thr Trp Lys Asp His Arg Leu Arg Leu Pro Glu Asn Met Thr
                85                  90                  95

Gln Glu Tyr Arg Leu Leu Glu Val Asp Trp Leu Lys Asn Met Trp Arg
            100                 105                 110

Pro Asp Ser Phe Phe Lys Asn Ala Lys Ser Val Thr Phe Gln Thr Met
        115                 120                 125

Thr Ile Pro Asn His Tyr Met Trp Leu Tyr Lys Asp Lys Thr Ile Leu
    130                 135                 140

Tyr Met Val Lys Leu Thr Leu Lys Leu Ser Cys Ile Met Asn Phe Ala
145                 150                 155                 160

Ile Tyr Pro His Asp Thr Gln Glu Cys Lys Leu Gln Met Glu Ser Leu
                165                 170                 175

Ser His Thr Thr Asp Asp Leu Ile Phe Gln Trp Asp Pro Thr Thr Pro
            180                 185                 190

Leu Val Val Asp Glu Asn Ile Glu Leu Pro Gln Val Ala Leu Ile Arg
        195                 200                 205
```

```
Asn Glu Thr Ala Asp Cys Thr Gln Val Tyr Ser Thr Gly Asn Phe Thr
    210                 215                 220

Cys Leu Glu Val Val Phe Thr Leu Lys Arg Arg Leu Val Tyr Tyr Val
225                 230                 235                 240

Phe Asn Thr Tyr Ile Pro Thr Cys Met Ile Val Met Ser Trp Val
                245                 250                 255

Ser Phe Trp Ile Lys Pro Glu Ala Ala Pro Ala Arg Val Thr Leu Gly
                260                 265                 270

Val Thr Ser Leu Leu Thr Leu Ser Thr Gln His Ala Lys Ser Gln Ser
        275                 280                 285

Ser Leu Pro Pro Val Ser Tyr Leu Lys Ala Val Asp Ala Phe Met Ser
        290                 295                 300

Val Cys Thr Val Phe Val Phe Met Ala Leu Met Glu Tyr Cys Leu Ile
305                 310                 315                 320

Asn Ile Val Leu Ser Asp Thr Pro Ile Pro Lys Pro Met Ala Tyr Pro
                325                 330                 335

Pro Lys Pro Val Ala Gly Asp Gly Pro Lys Lys Glu Gly Glu Gly Ala
                340                 345                 350

Pro Pro Gly Gly Ser Asn Ser Thr Ala Ser Lys Gln Gln Ala Thr Met
        355                 360                 365

Leu Pro Leu Ala Asp Glu Lys Ile Glu Lys Ile Glu Lys Ile Phe Asp
        370                 375                 380

Glu Met Thr Lys Asn Arg Arg Ile Val Thr Thr Thr Arg Arg Val Val
385                 390                 395                 400

Arg Pro Pro Leu Asp Ala Asp Gly Pro Trp Ile Pro Arg Gln Glu Ser
                405                 410                 415

Arg Ile Ile Leu Thr Pro Thr Ile Ala Pro Pro Pro Pro Pro Pro Gln
                420                 425                 430

Pro Ala Ala Pro Glu Pro Glu Leu Pro Lys Pro Lys Leu Thr Pro Ala
        435                 440                 445

Gln Glu Arg Leu Lys Arg Ala Ile Tyr Ile Asp Arg Ser Ser Arg Val
        450                 455                 460

Leu Phe Pro Ala Leu Phe Ala Ser Leu Asn Gly Ile Tyr Trp Cys Val
465                 470                 475                 480

Phe Tyr Glu Tyr Leu
                485

<210> SEQ ID NO 8
<211> LENGTH: 19
<212> TYPE: DNA
<213> ORGANISM: Artificial Sequence
<220> FEATURE:
<223> OTHER INFORMATION: oligonucleotide

<400> SEQUENCE: 8
cttgcacaaa gctggcgtg                                           19

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
gtgagcagta tcgcatattg                                          20
```

<210> SEQ ID NO 10
<211> LENGTH: 22
<212> TYPE: DNA
<213> ORGANISM: Artificial Sequence
<220> FEATURE:
<223> OTHER INFORMATION: oligonucleotide

<400> SEQUENCE: 10
gtagttattt gatatgtcta gc                                    22

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
acctgttgag tactctatag                                       20

<210> SEQ ID NO 12
<211> LENGTH: 19
<212> TYPE: DNA
<213> ORGANISM: Artificial Sequence
<220> FEATURE:
<223> OTHER INFORMATION: oligonucleotide

<400> SEQUENCE: 12
tttgcacaga cgtggaagg                                        19

<210> SEQ ID NO 13
<211> LENGTH: 19
<212> TYPE: DNA
<213> ORGANISM: Artificial Sequence
<220> FEATURE:
<223> OTHER INFORMATION: oligonucleotide

<400> SEQUENCE: 13
acaggaatac cgcctgctc                                        19

<210> SEQ ID NO 14
<211> LENGTH: 21
<212> TYPE: DNA
<213> ORGANISM: Artificial Sequence
<220> FEATURE:
<223> OTHER INFORMATION: oligonucleotide

<400> SEQUENCE: 14
ttcatttcgg atgagggcca c                                     21

<210> SEQ ID NO 15
<211> LENGTH: 26
<212> TYPE: DNA
<213> ORGANISM: Artificial Sequence
<220> FEATURE:
<223> OTHER INFORMATION: oligonucleotide

<400> SEQUENCE: 15
catcttcctt gcacaaagct ggcgtg                                26

<210> SEQ ID NO 16
<211> LENGTH: 25
<212> TYPE: DNA
<213> ORGANISM: Artificial Sequence
<220> FEATURE:
<223> OTHER INFORMATION: oligonucleotide

<400> SEQUENCE: 16
catgagtgag cagtatcgca tattg							25

<210> SEQ ID NO 17
<211> LENGTH: 26
<212> TYPE: DNA
<213> ORGANISM: Artificial Sequence
<220> FEATURE:
<223> OTHER INFORMATION: oligonucleotide

<400> SEQUENCE: 17
tgtgttcttt gcacagacgt ggaagg						26

<210> SEQ ID NO 18
<211> LENGTH: 25
<212> TYPE: DNA
<213> ORGANISM: Artificial Sequence
<220> FEATURE:
<223> OTHER INFORMATION: oligonucleotide

<400> SEQUENCE: 18
tatgacacag gaataccgcc tgctc							25

<210> SEQ ID NO 19
<211> LENGTH: 28
<212> TYPE: DNA
<213> ORGANISM: Artificial Sequence
<220> FEATURE:
<223> OTHER INFORMATION: oligonucleotide

<400> SEQUENCE: 19
gtctagctgc ggcaactcaa tctccgtg						28

<210> SEQ ID NO 20
<211> LENGTH: 28
<212> TYPE: DNA
<213> ORGANISM: Artificial Sequence
<220> FEATURE:
<223> OTHER INFORMATION: oligonucleotide

<400> SEQUENCE: 20
ctcgatcatc atggagcaga tttgcgtg						28

<210> SEQ ID NO 21
<211> LENGTH: 27
<212> TYPE: DNA
<213> ORGANISM: Artificial Sequence
<220> FEATURE:
<223> OTHER INFORMATION: oligonucleotide

<400> SEQUENCE: 21
cgccgtttca tttcggatga gggccac						27

<210> SEQ ID NO 22
<211> LENGTH: 28
<212> TYPE: DNA
<213> ORGANISM: Artificial Sequence
<220> FEATURE:
<223> OTHER INFORMATION: oligonucleotide

<400> SEQUENCE: 22
caggctttcc atttgcagct tgcactcc						28

<210> SEQ ID NO 23

```
<211> LENGTH: 23
<212> TYPE: DNA
<213> ORGANISM: Artificial Sequence
<220> FEATURE:
<223> OTHER INFORMATION: oligonucleotide

<400> SEQUENCE: 23
caatcgtcgc gataactctg ccg                                              23

<210> SEQ ID NO 24
<211> LENGTH: 27
<212> TYPE: DNA
<213> ORGANISM: Artificial Sequence
<220> FEATURE:
<223> OTHER INFORMATION: oligonucleotide

<400> SEQUENCE: 24
cctttattta tacactacat ggtaatc                                          27

<210> SEQ ID NO 25
<211> LENGTH: 24
<212> TYPE: DNA
<213> ORGANISM: Artificial Sequence
<220> FEATURE:
<223> OTHER INFORMATION: oligonucleotide

<400> SEQUENCE: 25
tgtttacgct ctattccttc ggag                                             24

<210> SEQ ID NO 26
<211> LENGTH: 23
<212> TYPE: DNA
<213> ORGANISM: Artificial Sequence
<220> FEATURE:
<223> OTHER INFORMATION: oligonucleotide

<400> SEQUENCE: 26
aactgccaag acgtttagaa cgg                                              23

<210> SEQ ID NO 27
<211> LENGTH: 26
<212> TYPE: DNA
<213> ORGANISM: Artificial Sequence
<220> FEATURE:
<223> OTHER INFORMATION: oligonucleotide

<400> SEQUENCE: 27
cgagtaaact gttaaatgct gaagtg                                           26

<210> SEQ ID NO 28
<211> LENGTH: 25
<212> TYPE: DNA
<213> ORGANISM: Artificial Sequence
<220> FEATURE:
<223> OTHER INFORMATION: oligonucleotide

<400> SEQUENCE: 28
tacaattcac ttaggctaca tcagc                                            25

<210> SEQ ID NO 29
<211> LENGTH: 23
<212> TYPE: DNA
<213> ORGANISM: Artificial Sequence
<220> FEATURE:
<223> OTHER INFORMATION: oligonucleotide

<400> SEQUENCE: 29
```

```
ggctacatca gctactacgt cac                                              23

<210> SEQ ID NO 30
<211> LENGTH: 42
<212> TYPE: DNA
<213> ORGANISM: Artificial Sequence
<220> FEATURE:
<223> OTHER INFORMATION: oligonucleotide

<400> SEQUENCE: 30
taatacgact cactataggg agggtgttca taatgcaaag cc                         42

<210> SEQ ID NO 31
<211> LENGTH: 43
<212> TYPE: DNA
<213> ORGANISM: Artificial Sequence
<220> FEATURE:
<223> OTHER INFORMATION: oligonucleotide

<400> SEQUENCE: 31
tttttttttt tttttttttt cataggaacg ttgtccaata gac                        43

<210> SEQ ID NO 32
<211> LENGTH: 41
<212> TYPE: DNA
<213> ORGANISM: Artificial Sequence
<220> FEATURE:
<223> OTHER INFORMATION: oligonucleotide

<400> SEQUENCE: 32
taatacgact cactataggg aggcacatta aaatggtgtt c                          41

<210> SEQ ID NO 33
<211> LENGTH: 41
<212> TYPE: DNA
<213> ORGANISM: Artificial Sequence
<220> FEATURE:
<223> OTHER INFORMATION: oligonucleotide

<400> SEQUENCE: 33
tttttttttt tttttttttt ccttatagat actcgtagaa c                          41
```